United States Patent
Fontaine et al.

(10) Patent No.: US 11,872,068 B2
(45) Date of Patent: Jan. 16, 2024

(54) PULSED X-RAY IMAGING

(71) Applicant: SOCPRA SCIENCES ET GÉNIE S.E.C., Sherbrooke (CA)

(72) Inventors: Rejean Fontaine, Sherbrooke (CA); Julien Rossignol, Sherbrooke (CA); Yves Bérubé-Lauzière, Sherbrooke (CA)

( * ) Notice: Subject to any disclaimer, the term of this patent is extended or adjusted under 35 U.S.C. 154(b) by 335 days.

(21) Appl. No.: 17/290,815

(22) PCT Filed: Oct. 29, 2019

(86) PCT No.: PCT/CA2019/051521
§ 371 (c)(1),
(2) Date: May 3, 2021

(87) PCT Pub. No.: WO2020/093140
PCT Pub. Date: May 14, 2020

(65) Prior Publication Data
US 2021/0369222 A1 Dec. 2, 2021

Related U.S. Application Data

(60) Provisional application No. 62/755,813, filed on Nov. 5, 2018.

(51) Int. Cl.
*A61B 6/00* (2006.01)
*G01T 1/17* (2006.01)
(Continued)

(52) U.S. Cl.
CPC ............ *A61B 6/483* (2013.01); *A61B 6/4085* (2013.01); *A61B 6/4241* (2013.01); *G01T 1/17* (2013.01); *H01J 35/065* (2013.01); *H05G 1/085* (2013.01)

(58) Field of Classification Search
CPC ....... G01T 1/17; G01T 1/2914; G01T 1/2985; G01T 1/29; G01T 1/1648; A61B 6/4085;
(Continued)

(56) References Cited

U.S. PATENT DOCUMENTS 5,519,227 A * 5/1996 Karellas .................. G01T 1/202
250/483.1
5,999,836 A   12/1999 Nelson et al.
(Continued)

FOREIGN PATENT DOCUMENTS

JP   2000-187077 A   7/2000
JP   2001-155897 A   6/2001
(Continued)

OTHER PUBLICATIONS

European application No. 19882323.9 extended European search report dated Nov. 2, 2021.
(Continued)

*Primary Examiner* — Irakli Kiknadze

(57) ABSTRACT

The X-ray imager combines a pulsed X-ray source with a time-sensitive X-ray detector to provide a measure of ballistic photons with a reduction of scattered photons. The imager can provide a comparable contrast-to-noise X-ray image using significantly less radiation exposure than conventional X-ray imagers, notably about half of the radiation.

18 Claims, 13 Drawing Sheets

(51) Int. Cl.
*H01J 35/06* (2006.01)
*H05G 1/08* (2006.01)

(58) Field of Classification Search
CPC ..... A61B 6/5282; A61B 6/4241; A61B 6/032;
A61B 6/483; A61B 6/4233; A61B
6/5205; A61B 6/42; A61B 6/4429; A61B
5/0071; A61B 5/0073; A61B 6/54; A61B
6/4266; A61B 6/027; A61B 6/484; A61B
6/4028; A61B 6/542; A61B 6/06; A61B
6/482; A61B 6/4007; A61B 6/544; A61B
6/4014; A61B 6/486; A61B 6/481; A61B
6/4452; A61B 6/4078; A61B 6/4071;
A61B 6/025; A61B 6/585; A61B 6/52;
A61B 6/4035; A61B 6/14; A61B 6/4021;
A61B 6/405; A61B 5/4547; A61B
6/5235; A61B 6/502; A61B 6/037; A61B
6/466; A61B 6/4258; A61B 6/545; H01J
35/065; H05G 1/085; H05G 2/00; H05G
2/008; G01N 2223/419; G01N 2223/204;
G01N 21/4795; G01N 21/6428; G01N
21/6456; G01N 2021/6439; G01N
2223/423; G01N 23/087; G01N 23/04;
G01N 9/24; G01N 2223/206; G01N
2223/405; G01N 2223/408; G01N
2223/501; H04B 10/70; H01L 31/107;
A61K 49/0409; A61C 19/04; G21K 1/02;
G21K 1/043; H01S 3/0085; H01S
3/10015; H01S 3/1003
USPC .............................. 378/4, 19, 98.9, 62, 6, 7
See application file for complete search history.

(56) References Cited

U.S. PATENT DOCUMENTS

| 10,134,571 | B1* | 11/2018 | Norberg | H01J 47/022 |
|---|---|---|---|---|
| 2002/0057760 | A1 | 5/2002 | Carroll et al. | |
| 2009/0022264 | A1 | 1/2009 | Zhou et al. | |
| 2009/0238330 | A1* | 9/2009 | Luhta | A61B 6/032 |
| | | | | 378/19 |
| 2011/0007869 | A1* | 1/2011 | Gendreau | G01N 23/20 |
| | | | | 378/46 |
| 2014/0321862 | A1 | 10/2014 | Frohlch et al. | |
| 2015/0196201 | A1 | 7/2015 | Andersson Engels et al. | |
| 2016/0187269 | A1* | 6/2016 | Brady | G01N 23/207 |
| | | | | 378/87 |
| 2017/0219501 | A1 | 8/2017 | Yakimov et al. | |
| 2017/0241920 | A1 | 8/2017 | Barty | |

FOREIGN PATENT DOCUMENTS

| JP | 2005-185574 A | 7/2005 |
|---|---|---|
| WO | 01/19143 A1 | 3/2001 |

OTHER PUBLICATIONS

Gratz Matthias et al: "Time-gated imaging in planar and tomographic x-ray imaging", Medical Physics, AIP, Melville, NY, US, vol. 26, No. 3, Mar. 1, 1999 (Mar. 1, 1999), pp. 438-446, XP012010731, ISSN: 0094-2405, D0I: 10.1118/1.598535.
Matthias Gratz et al: "Time gated imaging in radiology: theoretical and experimental studies", IEEE Journal of Selected Topics in Quantum Electronics, IEEE Service Center, Piscataway, NJ, US, vol. 2, No. 4, Dec. 1, 1996 (Dec. 1, 1996), XP011062139, ISSN: 1077-260X.
Andre Egbert, Boris N. Chichkov: Compact electron-based EUV and ultrashort hard x-ray sources SPIE, PO Box 10 Bellingham WA 98227-0010 USA, vol. 5196, Jan. 7, 2004 (Jan. 7, 2004), pp. 244-255, XP040251974, DOI: 10.1117/12.499589.
Ghani et al., "Characterization of continuous and pulsed emission modes of a hybrid micro focus x-ray source for medical imaging applications"; Nuclear Instruments and Methods in Physics Research Section A: Accelerators, Spectrometers, Detectors and Associated Equipment, vol. 853, May 1, 2017, pp. 70-77.
Meijlink, J. R. et al., "First measurement of scintillation photon arrival statistics using a high-granularity solid-state photosensor enabling time stamping of up to 20,480 single photons"; 2011; IEEE Nuclear Science Symposium Conference Record; Published in: 2011 IEEE Nuclear Science Symposium Conference Record;Date of Conference: Oct. 23-29, 2011; Date Added to IEEE Xplore: Feb. 21, 2012; DOI: 10.1109/NSSMIC.2011.6152491; pp. 2254-2257.
Barrett et al., 2004. "Education Exhibit Artifacts in CT: Recog-Nition and Avoidance 1." RadioGraphics. www.rsna.org (Oct. 29, 2018).
Derenzo, S. E. et al., 1994. "Design of a Pulsed X-Ray System for Fluorescent Lifetime Measurements with a Timing Accuracy of 109 Ps." IEEE Transactions on Nuclear Science.
Martin, Cj. 2007. "The Importance of Radiation Quality for Optimisation in Radiology." Biomedical imaging and intervention journal 3(2): e38. http://www.ncbi.nlm.nih.gov/pubmed/21614278 (Oct. 29, 2018).
Moses, W.W. et al. 1995. "Scintillator Characterization Using the LBL Pulsed X-Ray Facility." Radiation Measurements 24(4): 337-41. https://www.sciencedirect.com/science/article/abs/pii/135044879400111D (Oct. 29, 2018).
Parmee et al., 2015. "X-Ray Generation Using Carbon Nanotubes." Nano Convergence 2(1): 1. http://www.nanoconvergencejournal.com/content/2/1/1 (Oct. 29, 2018).
Rui, Xue et al. 2014. "Optimal KVp Selection for Contrast CT Imaging Based on a Projection-Domain Method." Conference proceedings. International Conference on Image Formation in X-Ray Computed Tomography 2014: 173-77. http://www.ncbi.nlm.nih.gov/pubmed/26413581 (Oct. 22, 2018).
Siewerdsen et al., 2001. "Cone-Beam Computed Tomography with a Flat-Panel Imager: Magnitude and Effects of x-Ray Scatter." Medical Physics 28(2): 220-31. http://doi.wiley.com/10.1118/1.1339879 (Apr. 25, 2017).
Von Der Linde, D et al. 2001. "Generation and Application of Ultrashort X-Ray Pulses". http://www.ilp.physik.uni-essen.de/vonderLinde/Publikationen/vonderLinde01LPB19_15.pdf (Oct. 29, 2018).
Webb, Steve. 1988. "The Physics of Medical Imaging". Hilger. https://www.crcpress.com/The-Physics-of-Medical-Imaging/Webb/p/book/9781439822081 (Apr. 2, 2017).
Wikimedia Commons. 2010. "Coolidge Side-Window Tube (Scheme) C: Filament/Cathode (−) A: Anode (+) Win and Wout: Water Inlet and Outlet of the Cooling Device." X-Ray Tube: https://en.wikipedia.org/wiki/X-ray_tube#/media/Fi, printed Apr. 26, 2021.
International application No. PCT/CA2019/051521 International Search Report dated Jan. 29, 2020.
International application No. PCT/CA2019/051521 Search Strategy dated Jan. 29, 2020.
International application No. PCT/CA2019/051521 Written Opinion of the International Searching Authority dated Jan. 29, 2020.
Corresponding Japanese patent application No. 2021-523961 Office Action dated Jul. 11, 2023.
Matthias Gratz et al., "Time-gated imaging in planar and tomographic x-ray imaging", Medical Physics Mar. 1999 vol. 26 No. 3 p. 438-446 DOI: 10.1118/1.598535.
Corresponding European patent application No. 19882323.9 Communication about intention to grant a European patent dated Jun. 23, 2023.

* cited by examiner

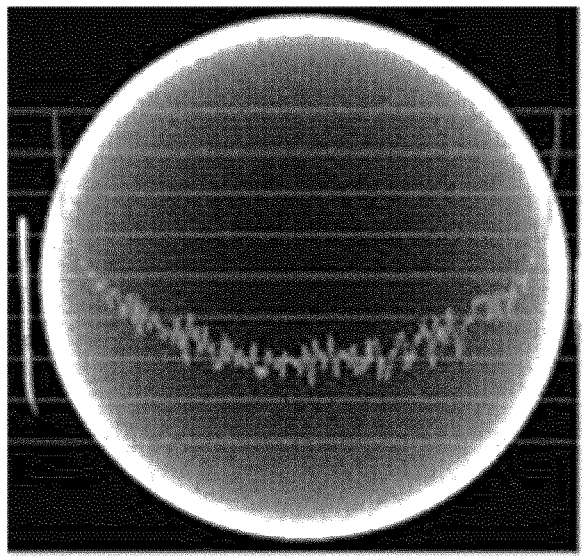
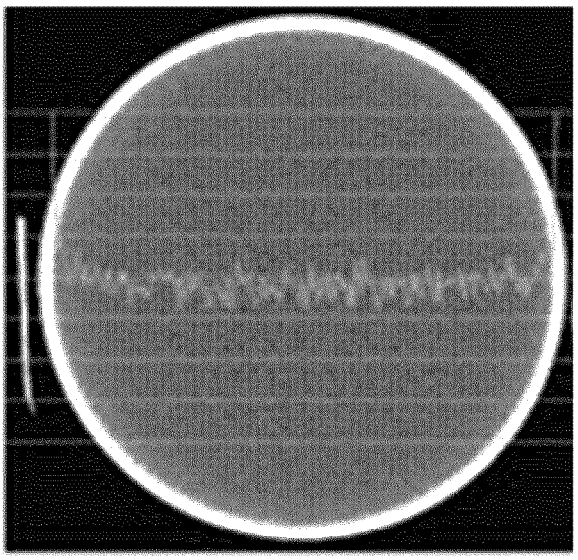
FIG. 3A
Prior Art
FIG. 3B
Prior Art
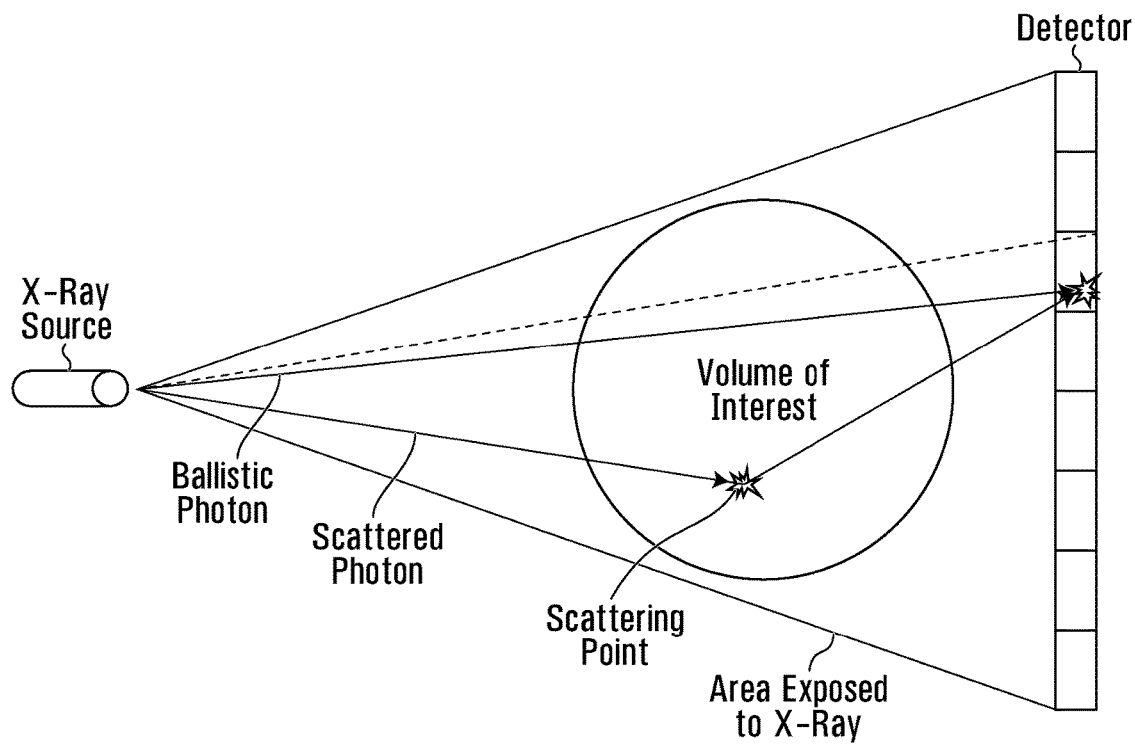
FIG. 4

FIG. 15
Prior Art
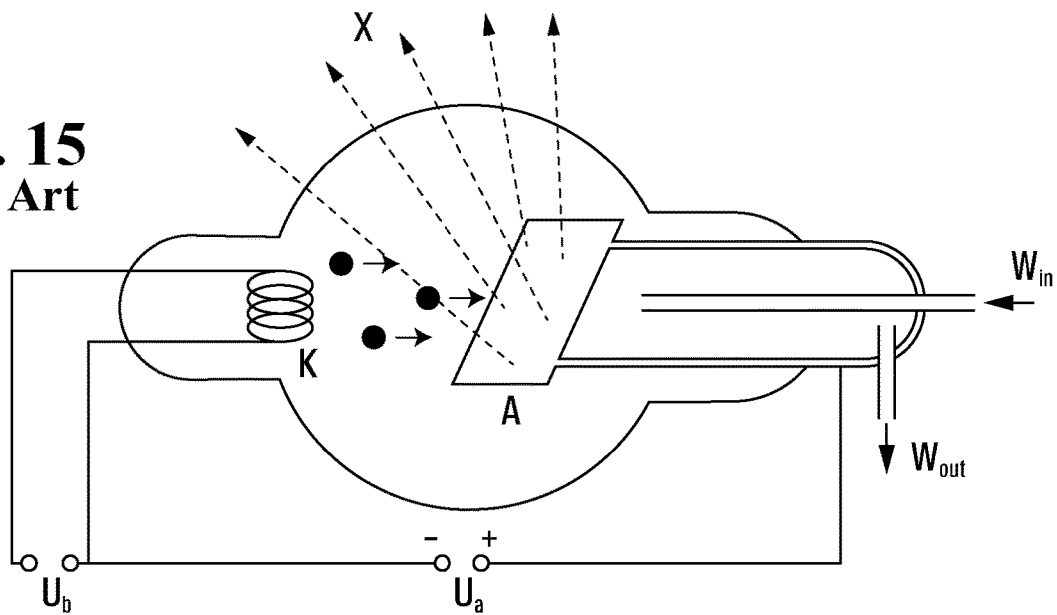
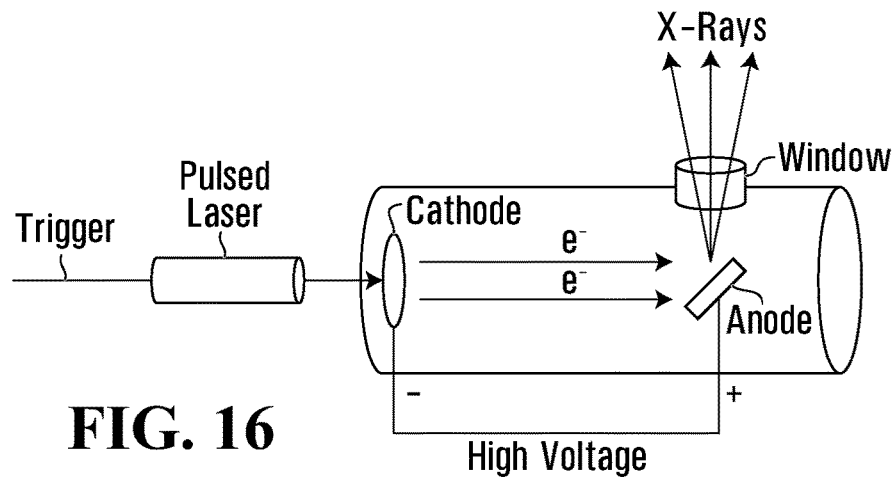
FIG. 16
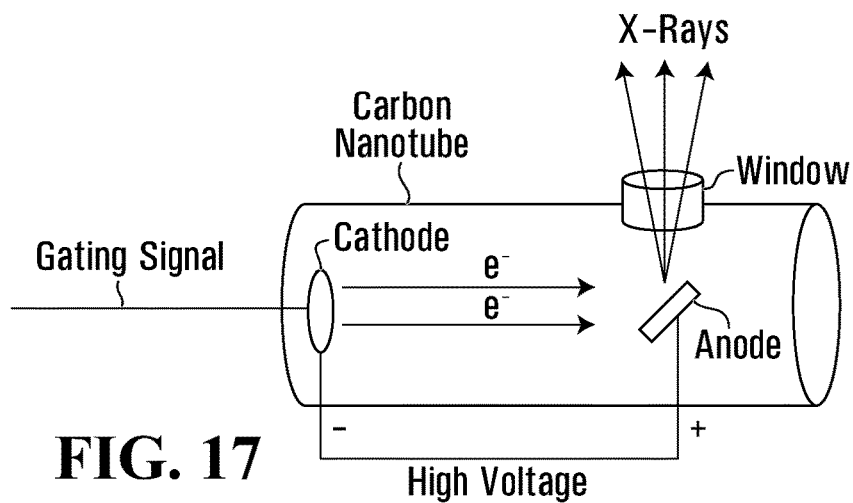
FIG. 17

PULSED X-RAY IMAGING

The present application claims priority from U.S. provisional patent application 62/755,813 filed Nov. 5, 2018, the specification of which is hereby incorporated by reference.

TECHNICAL FIELD

The present invention relates to X-ray and computed tomography (CT) imaging apparatus and methods.

BACKGROUND

X-ray imaging started with Rontgen's discovery of X-rays in 1895. X-ray imaging has greatly evolved towards more complex mechanisms able to obtain a spatial resolution as small as few microns. The principle underlying X-ray imaging relies on irradiating on one side a subject with X-rays produced by a source, and collecting, on the other side, onto a photographic plate or a digital recorder, the X-ray photons that have traveled through the subject.

In X-ray imaging, the image is formed thanks to absorption of the X-ray photons in the subject. The intensity of the absorbed photons gives an indication on the material density between the source and the detectors. Thus, X-ray imaging gives a 2D image of the density of the material in the subject. The raw image data is based on the photons that are not absorbed as they propagate from the source to the detector. If the object being imaged absorbs almost all the photons, imaging is either not possible or else most of the X-ray energy used is left in the patient, and likewise if the object being imaged fails to absorb a significant quantity of the photons, no imaging is possible. Low energy X-ray photons, that are less harmful to tissue, are easily absorbed by a given tissue thickness. High energy X-ray photons, that are more harmful to tissue, are less easily absorbed by a given tissue thickness. The energy of the photons is thus chosen for the object to be imaged to make sure that the relative loss of photons through absorption can provide useful imaging data.

Often a 3D image is important to obtain a better understanding of an anatomical abnormality and to perform an accurate medical diagnosis. The principle then relies on irradiating the subject at different angles around it with X-rays and acquire as many projections as required to reconstruct a slice of the subject with an appropriate image reconstruction algorithm as shown in FIG. 1. This principle, called computed tomography (CT), is highly used thanks to its low cost compared to other modalities such as magnetic resonance imaging (MRI) and to its high acquisition speed. CT is highly available around the world, and many improvements have been brought to it to optimize its overall performance.

Owing to the better understanding of the potential harmfulness of X-rays to living organisms, improvements in X-ray and CT mainly address the contrast-to-noise ratio (CNR) to dose tradeoff. The adverse effects of X-rays become even more important with recent research demonstrating the possibility of developing radiation-induced cancer where children are more likely affected. Moreover, children are also at a higher risk for passing any radiation-induced genetic defects to the next generation. Imaging protocols on children must always consider the lowest possible dose and special considerations must be taken into account whenever possible depending on the part of the body to be imaged. Although CT scans currently represent only 10% of all ionizing radiation-based imaging modalities, it delivers >50% of the collective dose for diagnostic imaging. One must now understand why pediatric CT imaging is made only when absolutely necessary. Small animal preclinical imaging is another important application of CT. At this level, the rat and the genetically modified mouse are chosen for their high genetic similarity to humans and for the ability to reproduce identical subjects at low cost. The variations in tissue density in these small animals is much smaller than for adult humans, and a high X-ray dose is mandatory to create a CNR high enough to differentiate cartilage/bones from fat and muscle. Thus, the dose used must carefully be chosen to avoid any radiation-induced cancer, genetic radiation-induced cancer or even worse, create a therapeutic effect on the lesion under study in such laboratory animals.

Image Contrast

Globally, X-ray absorption is described by a simple equation, namely the Beer-Lambert law:

$$L = L_0 e^{-\mu_l x},$$

where $L_0$ is the initial quantity of photons, $\mu_l$ the linear attenuation coefficient and x the distance traveled in the medium by the photons. More precisely, the absorption $\mu_l$ results from 3 physical phenomena and is given by:

$$\mu_l = \mu_{photoelectric} + \mu_{Compton} + \mu_{Rayleigh}.$$

Here, $\mu_{photoelectric}$ represents the portion of X-ray photons totally absorbed by atoms. A total absorption occurs when a photon collides with an electron close to the nucleus and ionizes the atom (hence the name photoelectric). As a result, the photon disappears, and an electron is then ejected and loses its energy in the surrounding material. This coefficient follows the relation $$\mu_{photoelectric} = \frac{Z_{eff}^3}{E^3}$$

where $Z_{eff}$ is the effective nuclear charge and E, the energy of the absorbed photon. The photoelectric effect is dominant at low X-ray energy. The coefficient $\mu_{Compton}$ accounts for Compton scattering which occurs when a photon interacts with an electron in the outer shells or that is weakly bonded to the nucleus. The effect looks like an elastic collision where the striking X photon transfers a part of its energy to the electron but continues its path at a different angle (the photon is not lost; it is just redirected). From a material point of view, the energy transfer can be seen as a partial absorption but from an image perspective, the scattered photon can hit the wrong detectors and adversely contribute to the signal by increasing the floor noise. The Compton scatter effect dominates for high Z materials or for high energy photons below 1 MeV. The last part of attenuation comes from Rayleigh scattering associated with the coefficient $\mu_{Rayleigh}$. Rayleigh scattering results from the interaction of the X-ray with an atom as a whole. The interaction modifies the electric field of the atom which in turn radiates at the same wavelength. Because of its low probability of occurring in the case of X-rays, this effect is of lesser interest here.

Since human tissues have $Z \approx 7.4$, the photoelectric effect dominates at up to 30 keV whereas Compton scattering dominates for X-ray energies >100 keV. When considering the subject volume, a minimal amount of X photon energy is required to make an image, and this is in the range 60-120 keV for humans and 30-80 keV for small animals. These ranges fall in the valley where the photoelectric effect (that provides useful information for imaging) ends and the Compton scattering increases. This problem is even amplified when increasing the X-ray energy over 120 keV where the probability of photoelectric absorption decreases while the probability of Compton scattering stays the same. This double effect increases the noise in integration-based X-ray detectors since the high energy photons contribute more to the accumulated energy while providing poor tissue absorption information and scattered photons increase the noise floor in images. Increasing the dose is the only way in integration-based X-ray imaging to improve the contrast in the image.

To better illustrate this phenomenon, FIG. 2A shows schematically photoelectric absorption and Compton scattering for bones and soft tissues as a function of X photon energy in the range of 30 to 120 keV. One can see that absorption is very high for the low energy photons and decreases significantly with higher energy. At 60 keV, the overall mass attenuation coefficient $\mu_t$ starts being dominated by Compton scattering. FIG. 2B shows schematically the relative dose delivered to a given patient at different tissue thicknesses as a function of X photon energy to obtain an image within a given acceptable CNR. As can be seen, thicker tissues require photons of higher energy to achieve the best possible dose-to-contrast ratio. At 140 keV, the higher Compton scattering contribution, compared to the photoelectric effect, decreases the contrast, as seen in FIG. 2A, that in turn, requires a longer exposure time for the same CNR than in thinner tissues. Hence, to image thicker tissues, such as the abdomen of bariatric patients, reducing the negative effect of scatter noise on CNR is required to reduce the dose. Furthermore, for a given CNR, there is a photon energy that will deliver the least amount of ionizing radiation to the tissues to obtain the image.

Many approaches have been proposed to reduce the dose deposited in a subject. Among them, one can reduce the X-ray energy to the minimum according to the patient weight or age, make a smaller region scan, determine the level of just acceptable noise to enable an adequate diagnostic ("present study indication"), avoid multiphase imaging (imaging more than once to see different details each time), and reduce overlapping of slices. Other approaches are to resort to tube current modulation, organ-based dose modulation, iterative reconstruction, spectral imaging (two or more X-ray energies), use of contrast agents, gating and photon counting with energy measurement. Except for the photon counting technique, all other approaches are suboptimal for dose reduction since the aforementioned problems are still present. The photon counting method with or without energy measurement is a technique already used in positron emission tomography (PET) where each annihilation gamma ray photon is timestamped along with an energy measurement to eliminate Compton scattering (Compton scattered photons have less energy). Since the source is monochromatic in PET (511 keV), Compton diffusion can be eliminated by applying an energy threshold. This is not the case in X-ray and CT since the X-ray source has a wide energy spectrum. Moreover, PET systems use large pixels >0.5×0.5 mm$^2$, that lead to an insufficient spatial resolution in X-ray CT and a limited count rate.

Cup artefacts as shown in FIG. 3 is a well-known problem in CT imaging. This problem occurs because X-rays crossing the central region of the subject have more chance to be absorbed than X-rays passing at the periphery. Similarly, X-rays passing through more tissue have more chance to be subjected to Compton scattering and thus adding noise to the image. The cup artefacts can be observed when imaging subjects of different thickness/diameter. At this level, bariatric patients will have more cup artefact than normal patients for identical imaging procedures.

SUMMARY

Applicant has discovered that contrast to noise in an X-ray image can be improved using a pulsed source of X-rays coupled with a detector that is time-sensitive so as to be able to detect ballistic photons without the background contribution of scattered photons.

In some embodiments, an X-ray imager combines a pulsed X-ray source with a time-sensitive X-ray detector to provide a measure of ballistic photons with a reduction of scattered photons. The imager can provide a comparable contrast-to-noise X-ray image using significantly less radiation exposure than conventional X-ray imagers, for example less than about half of the radiation.

The time resolution of the imaging apparatus is dependent on the sharpness of the rise time of the X-ray source and on the time resolution of the time-sensitive detector. More specifically, if the time resolution is less than about 0.9 nanoseconds, Applicant has found that the contrast to noise ratio (CNR) can be improved over continuous X-ray sources for most human patient imaging. While the rising edge of the X-ray pulse is preferably less than 0.15 nanoseconds, it will be appreciated that improvements in contrast can be achieved with rising edges up to about 0.5 nanoseconds. The pulsed X-ray source can have a Gaussian pulse shape with a full width half maximum (FWHM) value in the range of less than 0.1 nanoseconds up to about 0.5 nanoseconds.

As an example, one can measure the time resolution of an imaging apparatus by removing a subject or object from the apparatus and detecting one or more pulses by directly using the detector. This can be said to be a measure of the "impulse response" of the imaging apparatus which also corresponds to the response of the ballistic photons in a normal measurement, since there should be no scattered photons. Then, a time point or window parameter can be chosen to accept more or less of the ballistic/scattered photons according to the needs of the acquisition, either to improve the signal-to-noise ratio (SNR) by accepting all ballistic photons or to improve further CNR by cutting part of the ballistic photons to remove more scattered photons. Once a significant portion of scattered photons are removed from the raw image data to the benefit of detecting a greater percentage of ballistic photons, imaging quality can improve.

When the overall timing resolution of the system is better than about 300 picoseconds, the CNR can be at least about doubled for the same dose of radiation when imaging a typical thickness of 20 cm of tissue. With time resolution better than about 100 picoseconds, the amount of radiation delivered to the patient in abdominal imaging can be about 30% or less of the amount of radiation delivered to the patient for continuous, polychromatic X-ray imaging.

The innovation described herein presents a solution to both the limited count rate and the spatial resolution while significantly reducing the dose. The innovation herein described presents a solution to improve the cup artefact problem in bariatric human patients.

Applicant has found that an X-ray imaging apparatus can have a pulsed X-ray source having a control signal that determines the pulse timing and/or the pulse rise time. A time-sensitive X-ray detector can be included in the apparatus that has a time-dependent X-ray photon detection signal output. A processor, that can be connected to the control signal and the time-dependent X-ray photon detection signal output, can be configured to provide a measure of ballistic photons with a reduction of scattered photons received by the time-sensitive detector.

In some embodiments, the pulsed X-ray source may include a high voltage source, electrodes connected to the high voltage source for accelerating electrons, and an X-ray emitting target material arranged to receive the electrons following acceleration by the electrodes so as to produce a pulse of X-rays.

In some embodiments, the pulsed X-ray source may comprise a pulsed laser source responsive to the control signal, a photoelectric material arranged to receive a light pulse from the pulsed laser source and to emit a burst of electrons in response thereto, wherein electrodes are arranged to accelerate the burst of electrons. The photoelectric material may be at least a part of a cathode of the electrodes.

In some embodiments, the pulsed X-ray source may comprise deflection electrodes for steering the electrons accelerated by the electrodes connected to the high voltage source to controllably hit the X-ray emitting target material.

In some embodiments, the electrodes connected to the high voltage source comprise a gated carbon nanotube cathode.

In some embodiments, the time-sensitive X-ray detector provides for each photon detected at each pixel element a time of detection signal.

In some embodiments, the time-sensitive X-ray detector is responsive to a gate signal controlling a time when photon detection is enabled.

In some embodiments, the time-sensitive X-ray detector is responsive to a gate signal controlling a time when photon detection is disabled.

In some embodiments, the processor is configured to collect X-ray photons detected within different time frames with respect to the control signal and determine the measure of ballistic photons with a reduction of scattered photons received by the time-sensitive detector through subtraction of the X-ray photons detected within different time frames.

In some embodiments, the time-sensitive X-ray detector is responsive to a pulsed gate signal controlling a time window when photon detection is enabled.

In some embodiments, the time-sensitive X-ray detector is arranged with respect to the pulsed X-ray source so as to provide a different time of flight for the ballistic photons as a function of a pixel location within the time-sensitive X-ray detector, wherein the processor provides the measure of ballistic photons with the reduction of scattered photons received by the time-sensitive detector using different timing as a function of location of the pixels.

In some embodiments, the time-sensitive X-ray detector comprises an X-ray sensitive scintillator and a light sensor array coupled with the scintillator for measuring X-ray detection events in the scintillator.

In some embodiments, the time-sensitive X-ray detector comprises an X-ray sensitive detector based on a direct conversion of photons to electrons for measuring X-ray events in the detector.

In some embodiments, the processor is configured to provide a two-dimensional image.

In some embodiments, the apparatus can further comprise a motorized mounting for moving the pulsed X-ray source and the time-sensitive X-ray detector with respecting to an object or subject to be imaged, wherein the processor is configured to provide a three-dimensional image.

In some embodiments, the apparatus is operative to obtain an image with a given contrast to noise ratio (CNR) while delivering a lower dosage of X-rays to a typical human abdominal region of at least 20 cm thickness than when continuous X-rays of a same energy are used in a similarly-structured continuous X-ray imaging apparatus. The lower dosage may be at least 50% lower, preferably at least 60% lower.

In some embodiments, the pulsed X-ray source produces a cone beam and the time-sensitive X-ray detector is arranged to detect a 2D array of pixels.

In some embodiments, a response time of a combination of the pulsed X-ray source and the time-sensitive detector is less than 0.9 nanoseconds. Preferably, the response time is less than 0.3 nanoseconds. Preferably, a rise time of a pulse emitted by said pulsed X-ray source is less than 0.15 nanoseconds.

In some embodiments, the processor is configured to measure an impulse response time of a combination of the pulsed X-ray source and the time-sensitive detector to obtain a measure ballistic photons without an object or patient between the pulsed X-ray source and the time-sensitive detector and to derive therefrom and store in memory a gate parameter for the measure of ballistic photons with a reduction of scattered photons received by the time-sensitive detector when thereafter measuring objects or patients that provide scatter.

Applicant has also found a method of acquiring a medical diagnostic image of a human patient can comprises using an apparatus as described herein to obtain an image of a region of interest and having a contrast-to-noise ratio using X-rays of a given energy, wherein an amount of radiation delivered to the patient is about 60% or less of an amount of radiation delivered to a same patient for continuous, polychromatic X-ray imaging of the region of interest using the given energy of X-rays.

In some embodiments, the amount of radiation delivered to the patient is about 30% or less of an amount of radiation delivered to a same patient for continuous, polychromatic X-ray imaging of the region of interest using the given energy of X-rays.

BRIEF DESCRIPTION OF THE DRAWINGS

The invention will be better understood by way of the following detailed description of embodiments of the invention with reference to the appended drawings, in which:

FIG. 3A is an image showing cup artefacts with the intensity line profile superposed for heavy cup artefacts (Barrett & Keat, 2004);

FIG. 3B is an image showing cup artefacts with the intensity line profile superposed for no cup artefacts (Barrett & Keat, 2004);

FIG. 4 is a schematic diagram illustrating X-ray image acquisition showing ballistic and scattered photons travel for computed tomography (CT);

FIG. 15 is a schematic sectional side view of a conventional side-window type of X-ray tube having a water-cooled anode and a hot filament type cathode (Wikimedia Commons 2010);

FIG. 16 is a schematic sectional side view of a laser-pulsed cathode side-window type of X-ray tube;

FIG. 17 is a schematic sectional side view of a carbon nanotube (CNT) gated cathode side-window type of pulsed X-ray tube.

DETAILED DESCRIPTION

Figure 1A:
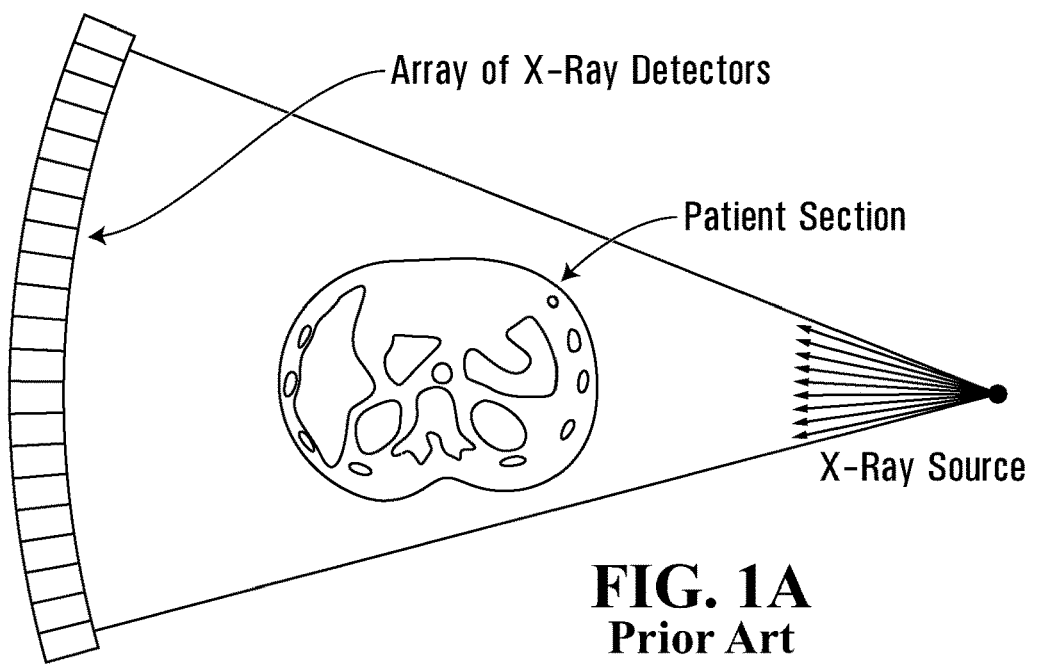
FIG. 1A is a schematic sectional view of a conventional arrangement of an X-ray source, array of X-ray detectors for a CT scanner with the object to be imaged shown as a patient section (Webb 1988)
Figure 1B:
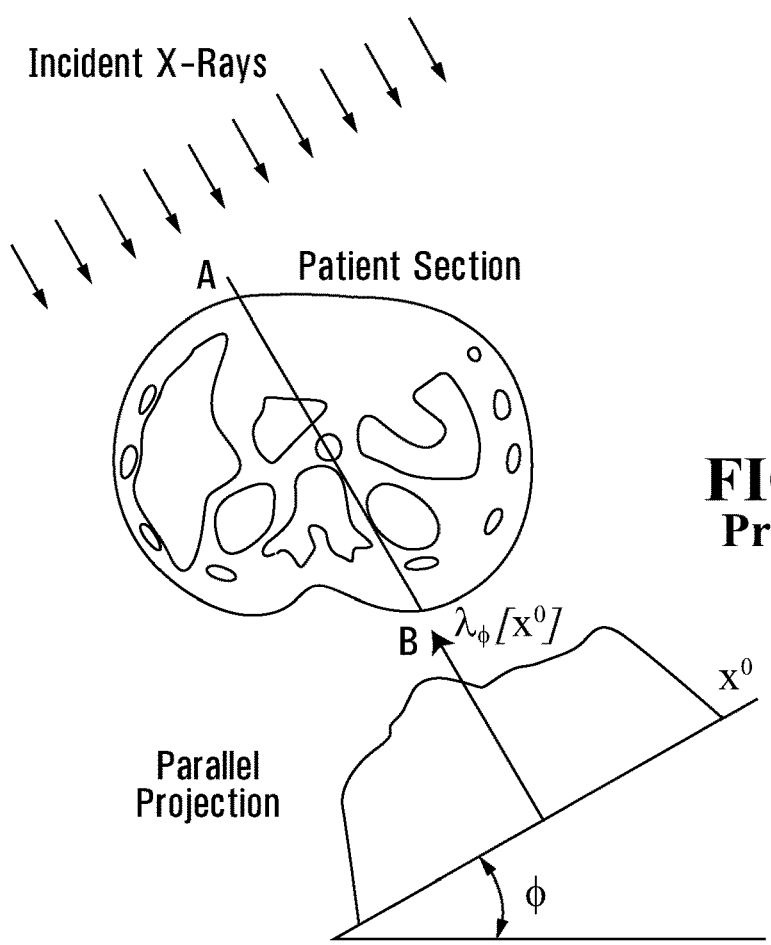
FIG. 1B is a schematic illustration of an image intensity profile acquired using the scanner of FIG. 1A (Webb 1988)
Figure 2A:
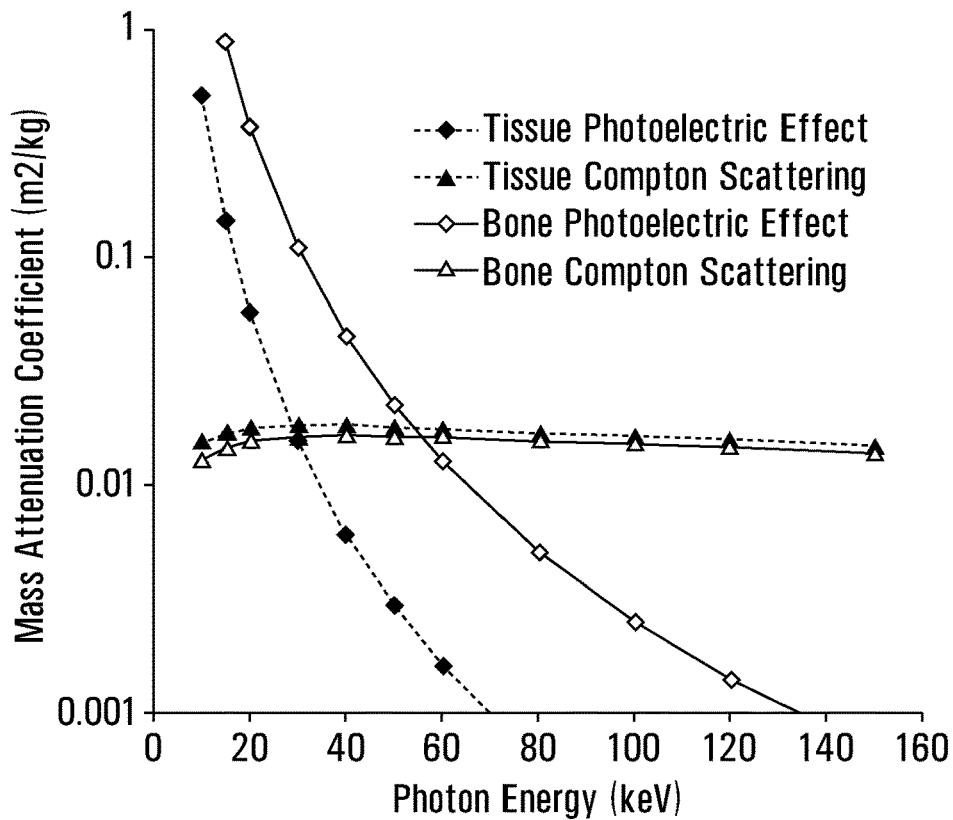
FIG. 2A is a plot showing Compton and photoelectric attenuation versus energy for bone and soft tissues (Martin 2007)
Figure 2B:
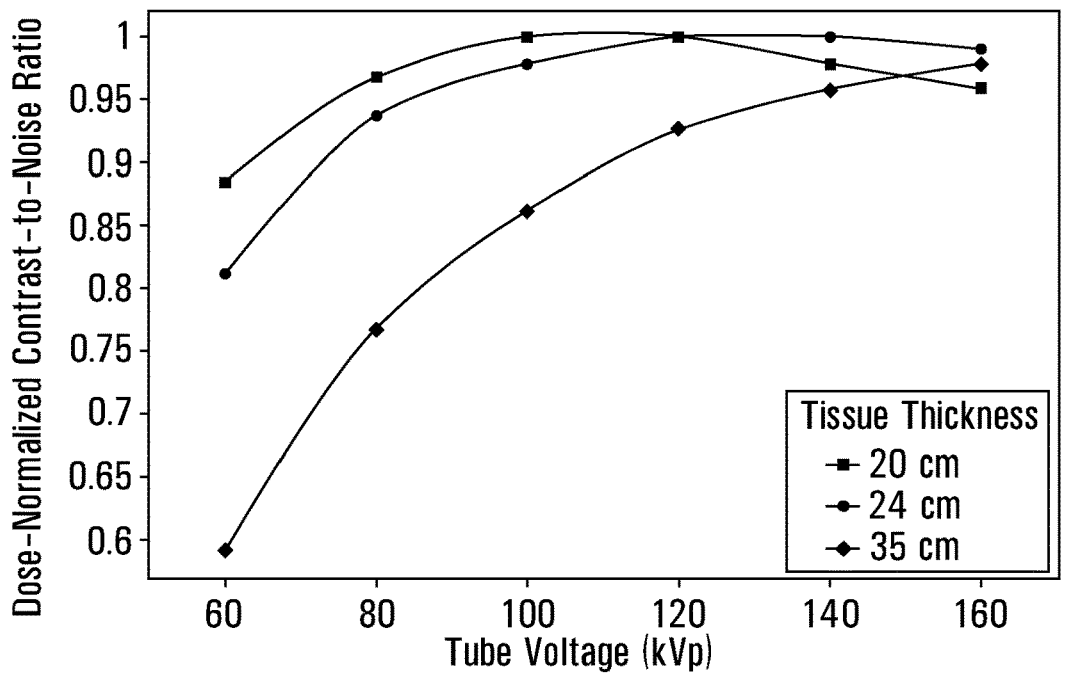
FIG. 2B is a plot showing the normalized CNR obtain with constant radiation exposure versus tube potential and tissue thickness. (Rui et al. 2014)

The present invention relates to separating diffused photons from ballistic photons by using photon time-of-flight (elapsed time from emission to detection) measurements. Currently, X-ray and CT imaging are mainly based on accumulating the energy of X-ray photons into pixels to create a 2D image or a slice of a 3D image. These approaches require a non-negligible dose to extract the useful signal from the background. The present invention proposes to measure the time of flight of X photons and directly sort the scattered photons from the ballistic ones. This will allow removing a substantial quantity of photons participating to the background noise of the image, as well as significantly attenuating the cup artefacts present in CT images. A significant dose reduction for a similar contrast can also be obtained, which is critical in several clinical uses of CT.

The approach to solving the aforementioned problems consists of measuring the time-of-flight (TOF) of each individual photon (or of a burst of photons) to determine whether a photon has followed a straight line ballistic trajectory or has been scattered. TOF is defined as the length of time between the photon's emission by the X-ray source and its arrival in the detection system where it is transduced into an electrical signal. In the X-ray wavelength range, the distance traveled by a photon is directly related to its TOF since the index of refraction is close to 1 and thus all photons have a speed close to the speed of light in a vacuum. Measuring TOF requires knowing when X photons leave the source and when they arrive in the detection system. A way to create such a condition can be to use ultra-short pulses of X photons to obtain a precise time of emission, and to measure the time of arrival of each individual photon or of the burst of photons resolved in time. For the types of tissue volumes encountered in human subjects (for example abdominal scans of children up to bariatric adults), improvement in image contrast can be achieved when time resolution is better than about 0.5 nanoseconds, and because a time resolution of at least about 0.2 nanoseconds is feasible using available technology, the improvement in contrast for a given dosage and/or the improvement in the reduction in dosage for a given contrast is significant.

Since scattered photons do not travel directly in straight line from the X-ray source to the detectors, their flight distance, therefore their TOF, is longer than that of ballistic photons as shown in FIG. 4. This is true for both Compton and Rayleigh scattered photons. For each pixel in the detection system, a maximum TOF for a ballistic photon is computed by dividing the longest distance from any point in the pixel to the X-ray source by the speed of light in a vacuum. Then, during scan, the detection system decides for each individual photon if the following condition is true:

$$\frac{d_{min}}{c} - \epsilon < T_{detection} - T_{emission} < \frac{d_{max}}{c} + W,$$

where $T_{detection}$ is the time of detection, $T_{emission}$ is the time of emission, $d_{max}$ and $d_{min}$ are respectively the maximum and minimum distances from the X-ray source to the detector pixel in which the photon is detected, c is the speed of light in vacuum, W and $\in$ form the limit of the accepted window of time respectively for the late and the early photons. If the previous condition is true, a photon is declared to be ballistic, otherwise it is declared to be scattered. The length of the time window (W+$\in$) must be chosen according to the spatial uncertainty of the measurements including the time resolution of the detection system, the time jitter of the X-ray source and the needs for the application. To select the optimal time window width, an acquisition can be made without any subject in the scanner to extract the impulse response of the system which also corresponds to the response of the ballistic photons in a normal measurement. Then, the window can be chosen to accept more or less of the ballistic/scattered photon according to the needs of the acquisition, either to improve SNR by accepting all ballistic photons or CNR by cutting part of the ballistic photons to remove more scattered photons. Window optimization will be presented later.

One of the most promising applications of TOF-X-ray imaging (whether 2D or 3D) is to remove photons identified as scattered photons from the measurements to reduce scatter noise and its adverse effect on image quality. This technique, that we call time-of-flight scatter rejection (TSR), can be implemented by gating the photons in the detection system. When the trigger, used for both the pulsed and the detection system, is received, the detection system time-stamps and/or counts the photons arriving in each pixel during a period of time in the selected time window. The scattered photons arriving too late (outside the time window) can be discarded from the measurements.

The temporal X-ray pulse width is preferably as narrow as possible to reduce the dose to the minimum. However, embodiments can operate with longer pulses to the detriment of the injected dose. In this case, late scattered photons are being discarded by the TSR along with most of the ballistic photon emitted the first few tenths of a picosecond after the pulse. The resulting signal is therefore composed mostly of ballistic photons, even though most of them are removed. This allows for CNR improvements at the cost of a higher dose. In all cases, the rising edge of the X-ray pulse must be as sharp as possible to reduce the timing jitter associated to the X-ray source.

Figure 5:
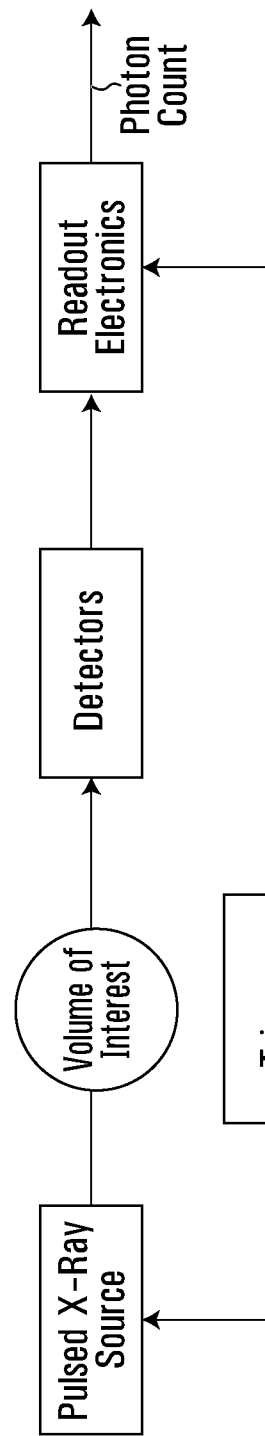
FIG. 5 is a block diagram of a time-of-flight (TOF) CT acquisition chain.

The required system for TOF-X-ray imaging (whether 2D or 3D) is essentially composed of four parts as shown in FIG. 5: a pulsed X-ray source, a detector, a gated electronic readout system and a synchronisation mechanism or trigger.

Any system able to precisely detect the time of arrival of X photons emitted by a pulsed source synchronized with the detectors' readout electronics could implement TOF-X-ray imaging (whether 2D or 3D). Herein, we propose an example of such a system, detailed in FIG. 6 and FIG. 7, to achieve a high enough time resolution and data throughput to successfully scan a subject using TSR. As an example, the system detailed in FIG. 6 and FIG. 7 could be implemented with a N5084 pulsed X-ray tube from Hamamatsu excited by a Picosecond light pulse PLP-10 from the same company, acting both as a pulsed laser and a trigger. The detection system can be implemented using a 500 μm thick LYSO crystal and a S12571-015C SiPM also from Hamamatsu. The readout circuit can be designed as an application specific integrated circuit (ASIC).

The output of the readout electronics can be subjected to additional digital processing such as finding centroid of events, data sorting and merging, data correction, dark noise filtering, etc. The output is TSR pixel data. An image processor generates 2D or 3D images from the pixel data using conventional techniques known in the art, however, without needing contrast improvement filters that might be conventionally employed. Such medical images can be viewed at an image viewing workstation as is known in the art.

Figure 12:
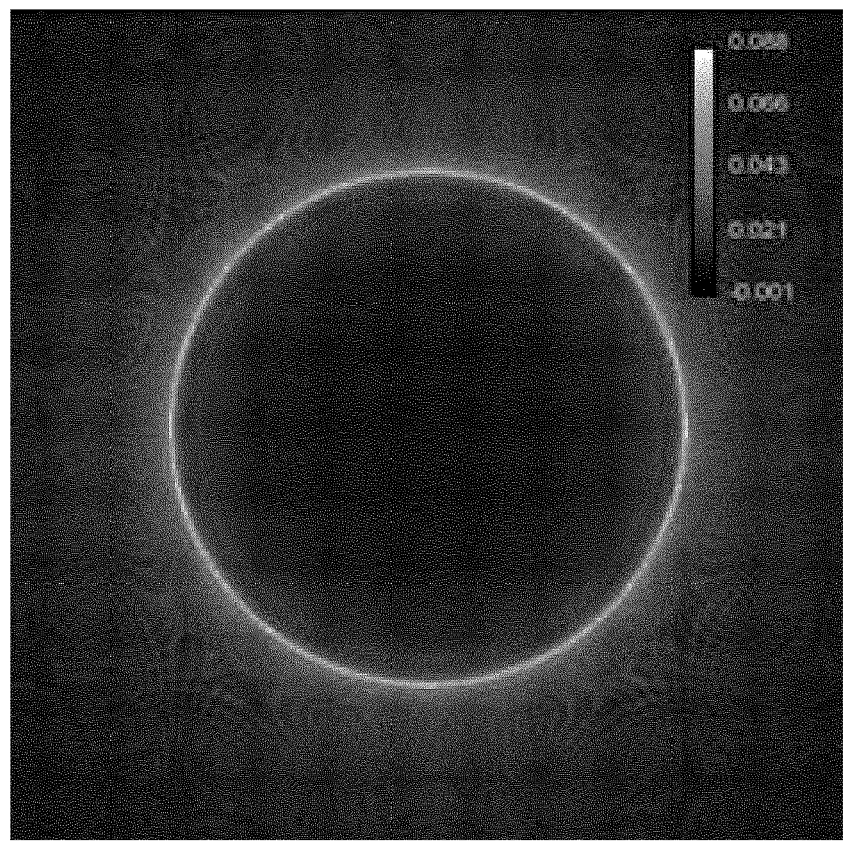
FIG. 12 is a simulated image showing only scattered photons removed by TSR in the image of FIG. 11A.

Since the number of scattered photons detected in each pixel is a function of the scattering ability of the object outside of the ballistic photon travel path, those photons can thus be considered as background noise. As the reconstructed image including scattered photon shows (FIG. 12), the contribution of those photons to the image is subject to a cup artifact. Moreover, the bone inserts are indistinguishable in this image, thus the scattered photons contribute negatively to the image contrast. The CNR is dependent on a statistically viable measurement of ballistic photons above the background. Assuming that the background is not spatially dependent (which it is), contrast is improved by collecting more photons, both ballistic and scattered, so that the spatial variation in ballistic photons provides a better CNR following a background subtraction. As can be appreciated, removing at least a portion of scattered photons using TSR reduces the need for collecting as many photons and improves image quality due to the non-uniform spatial distribution of scattered photons.

Multiple implementations of the X-ray source, described below, can generate suitably short pulses of X photons to reduce dosage while having a short enough rise time in intensity to allow for detection of ballistic photons and correspondingly provide the improvement in contrast. As an example, a trigger could be used to generate an ultra-short laser pulse directed onto the photocathode of an X-ray tube, generating a pulse of electrons accelerated in the tube with an electrical field. Similarly, an electron gun or canon could generate a continuous flow of electrons deflected or not on the X-ray emitter target. When the accelerated electrons hit the target then an X-ray pulse is generated towards the volume of interest using an aperture to form a fan or cone shaped beam.

The X-ray detector converts the photons into electric pulses. The detector is composed of a material with good X photon stopping power and able to generate low jitter electric pulses. The detector could be of any material for which the combination scintillating crystal/digital silicon photomultiplier is a good candidate, or alternatively a direct X-photon detector that can be gated with the desired time sensitivity.

Figure 6:
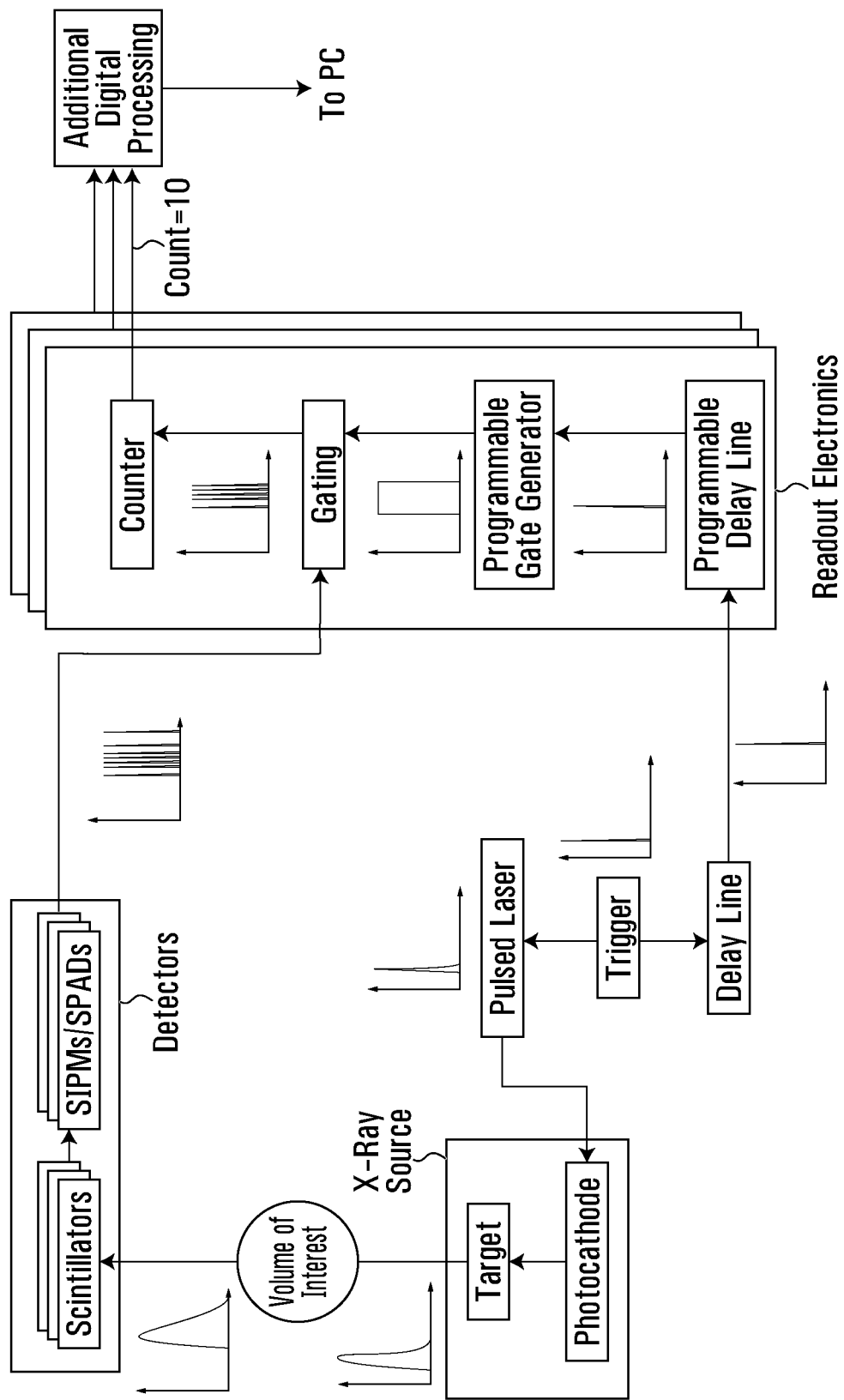
FIG. 6 is a detailed block representation of a TOF-CT acquisition chain with gating.
Figure 7:
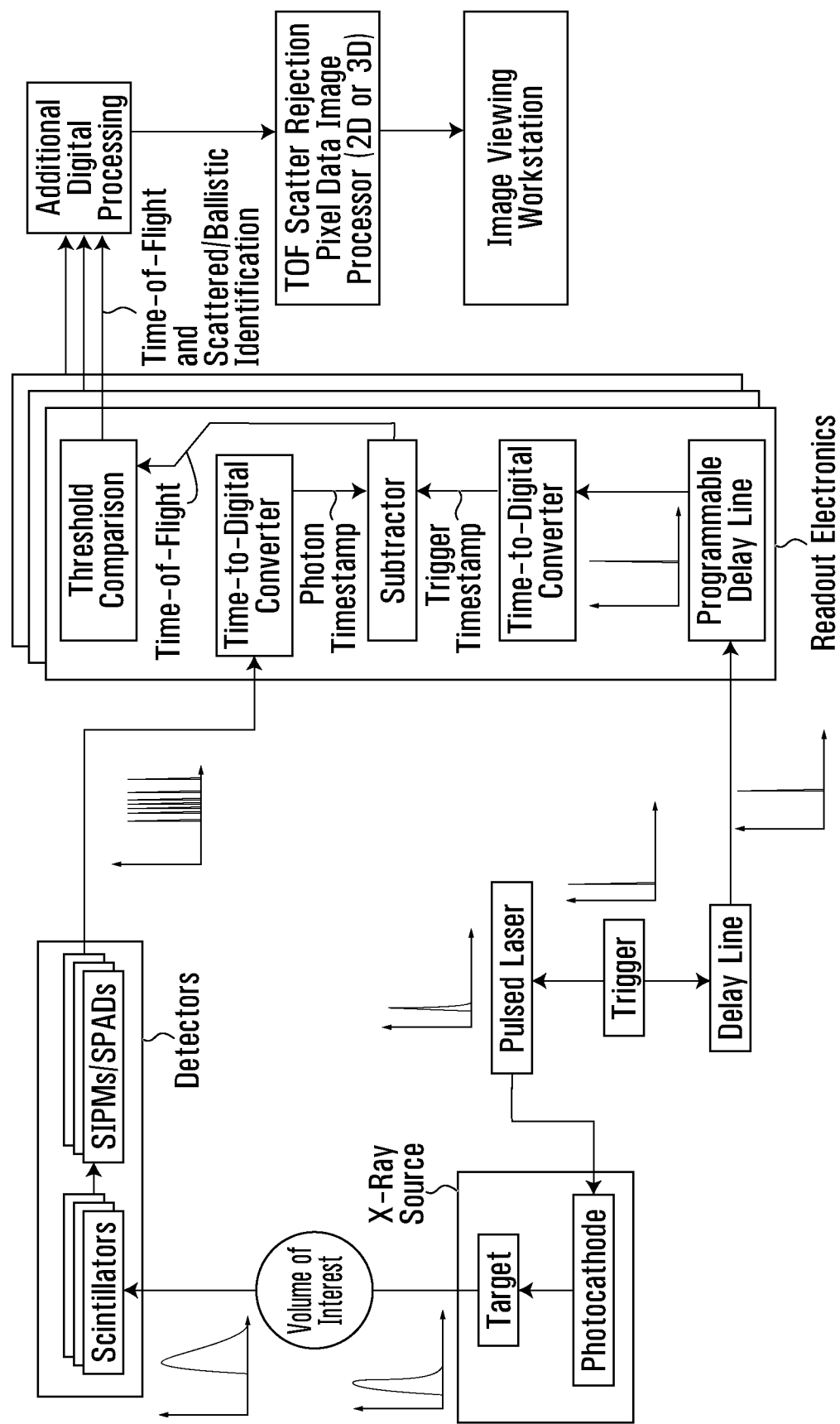
FIG. 7 is a detailed block representation of a TOF-CT acquisition chain with timestamps.

A brute force approach for the trigger could be an implementation where all detector pixels can individually time-stamp the time of arrival of each individual X photon (FIG. 7). A digital signal processor can then sort and compute the data to extract the relevant information. Another approach would be to electronically open a programmable or fixed time window directly within the detector. A trigger sent through a programmable or fixed delay line to the readout electronics of each pixel will initiate the acquisition. The timing window can then be adjusted to count only ballistic photons and remove the scattered photons (FIG. 6). This can be done by counting and localizing the photons detected during a number of X-ray pulses where the gating is set to capture the entire temporal point spread function (TPSF) followed by counting and localizing the photons detected during a number of different X-ray pulses where the gating is set to capture only the latter part of the TPSF, namely the non-ballistic photons, with the ballistic photon intensity being calculated by the difference between the full TPSF and the latter part of the TPSF. This requires a fast timing for switching on the acquisition without the need to have a fast response time for switching off photon detection.

The photon count in each pixel is finally sent to a centralized unit performing, if needed, additional digital signal processing before sending the data to a computer to perform image reconstruction in the case of computed tomography or to perform any desired image processing in the case of a 2D image.

As an example of this innovation, the Monte Carlo simulator GATE was used to simulate a cone-beam CT scanner with a flat panel detector system. In every simulation, a point source emits a continuous monochromatic beam of photons in an isotropic circular cone pattern towards a square flat panel array of detectors.

No energy measurements were done on individual photons, but those below 10 keV were automatically removed from the simulations. Both the time of emission and the time of detection provided by the simulator were used to measure the TOF of each photon and mimic a pulsed X-ray source. The effect of the pulse width was added to the emission time by randomly generating an offset using a probability distribution function of emission of the source over time. GATE was set up to compute time of detection according to the timestamp of the first event in a specific pixel associated with a single photon. At this point, it adds the effect of the time resolution of the detector system, always assumed to be Gaussian.

In Applicant's simulation, to measure performance of the TSR algorithm, the window was always placed within three standard deviations (3σ) of the total timing resolution (assumed to be Gaussian), to keep at least 99.5% of transmitted photons. For the single projection measurements for TSR validation, the source emits a 120 keV cone of X photons with an 8° angle. The phantom was placed 102 cm away from the source and a 256×256 array of 1×1 mm² pixels detector was placed 63 cm behind the phantom.

Figure 8:
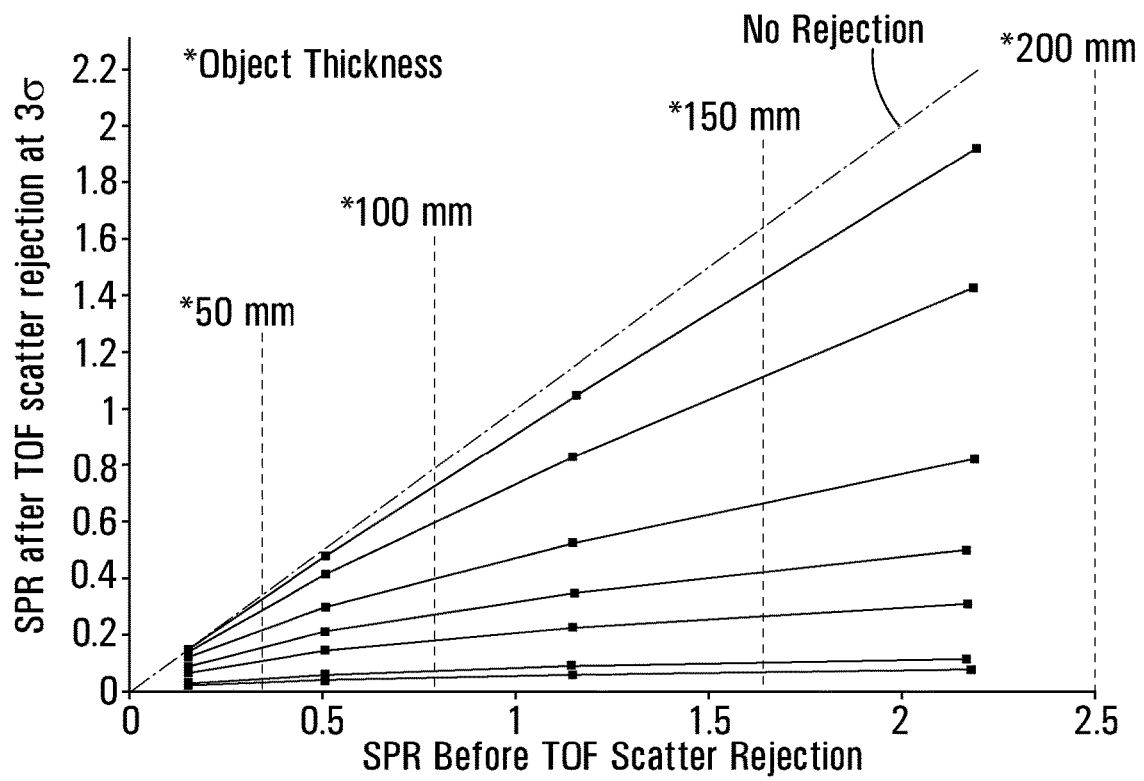
FIG. 8 is a plot showing scattered to primary radiation ratio (SPR) after ToF scatter rejection (TSR) as a function of SPR before TSR according to total time resolution for different object thicknesses (50 mm, 100 mm, 150 mm and 200 mm)
Figure 9A:
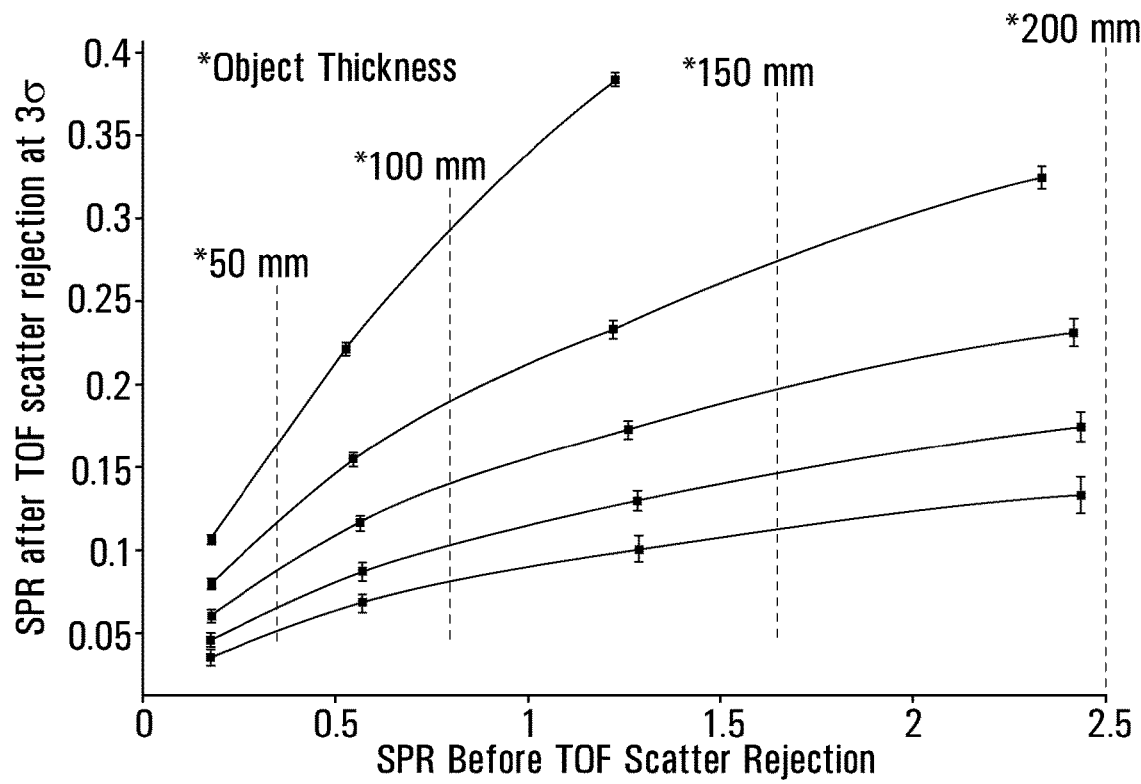
FIG. 9A is a plot showing SPR after TSR as a function of SPR before TSR for different object thicknesses (50 mm, 100 mm, 150 mm and 200 mm) and source to detector distances, namely 250 mm, 500 mm, 800 mm, 1200 mm and 1650 mm.
Figure 9B:
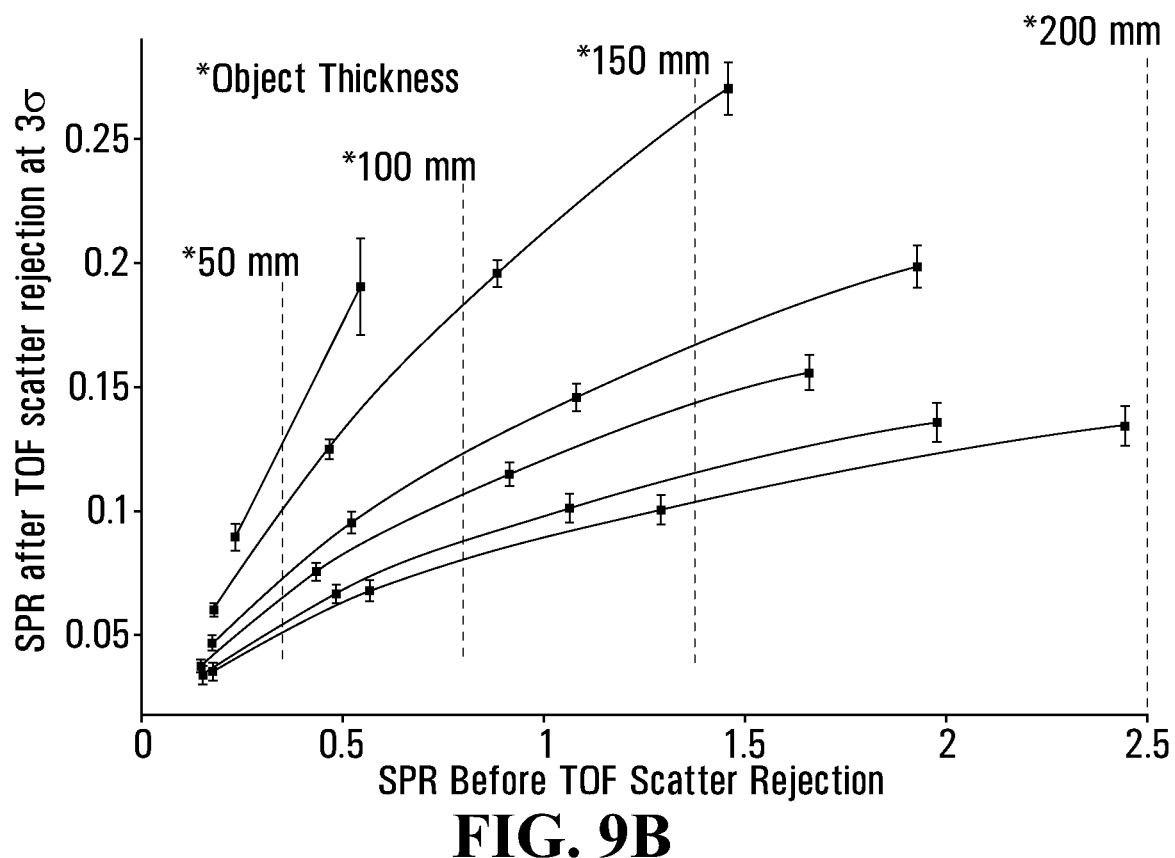
FIG. 9B is a plot showing SPR after TSR as a function of SPR before TSR for different object thicknesses (50 mm, 100 mm, 150 mm and 200 mm) and X photon energy, namely 20 keV, 40 keV, 60 keV, 80 keV, 100 keV and 120 keV.

The scattered to primary radiation ratio (SPR), is the energy of the scattered radiation (S) divided by the energy of the primary beam (P) striking the same point on the imaging device). The SPR after applying TSR for increasing initial SPR, obtained with 50, 100, 150 and 200 mm thick phantoms is presented in FIG. 8. Even with a total time resolution of 1 ns, improvements can be seen in some systems with both high incident photon energy and large source-to-detector distance. However, improving total timing resolution below 10 ps does not lead to significantly better results. As expected, the achieved SPR worsens with lower energies and smaller source-to-detector distance as seen in FIGS. 9A and 9B respectively.

Figure 11B:
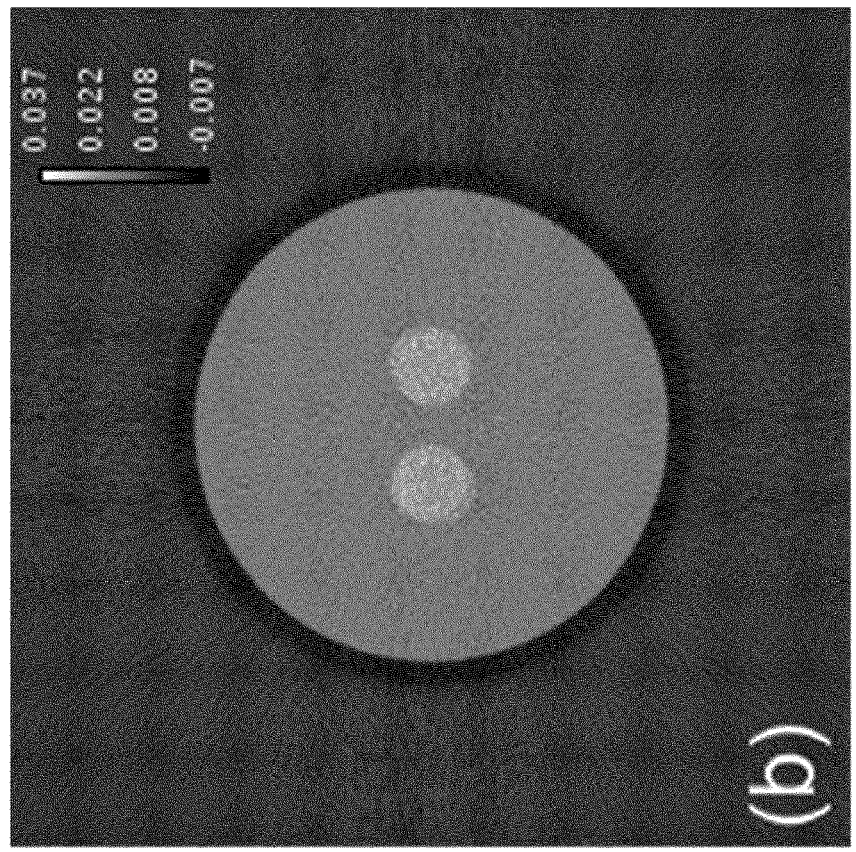
FIG. 11B is a simulated reconstructed image showing the effect of TSR on the contrast.
Figure 11A:
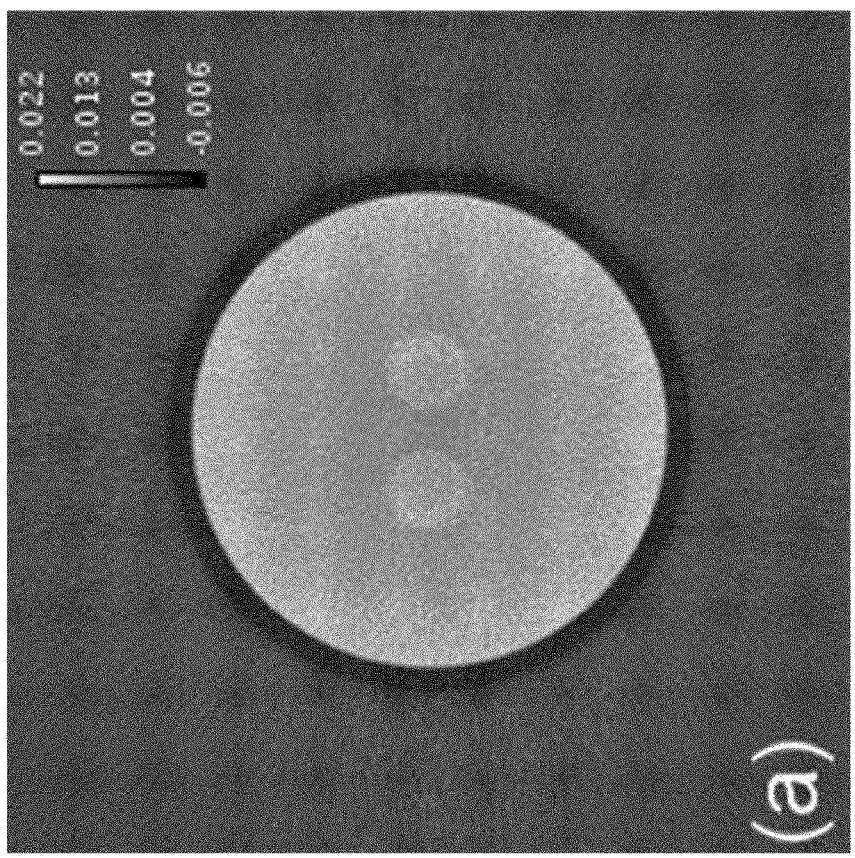
FIG. 11A is a comparative reconstructed image of the same object in FIG. 11B without applying TSR.

A slice of a reconstructed image of a 288 mm wide water cylinder with two bone inserts before and after applying TSR is shown in FIG. 11A and FIG. 11B respectively. The image was normalized then reconstructed by feeding the sinogram directly to the Reconstruction Toolkit (RTK) Feldkamp, Davis and Kress algorithm (FDK) with no additional processing. With a perfect timing resolution, 100 keV photon energy and 165 cm source-to-detector distance, SPR decreased from 300% to about 4% at the center of the detection system. The bone inserts are indistinguishable in the removed scattered photons image (FIG. 12) and a cup artifact is present. This explains the increase of contrast once those photons are removed from the reconstruction data.

Figure 13:
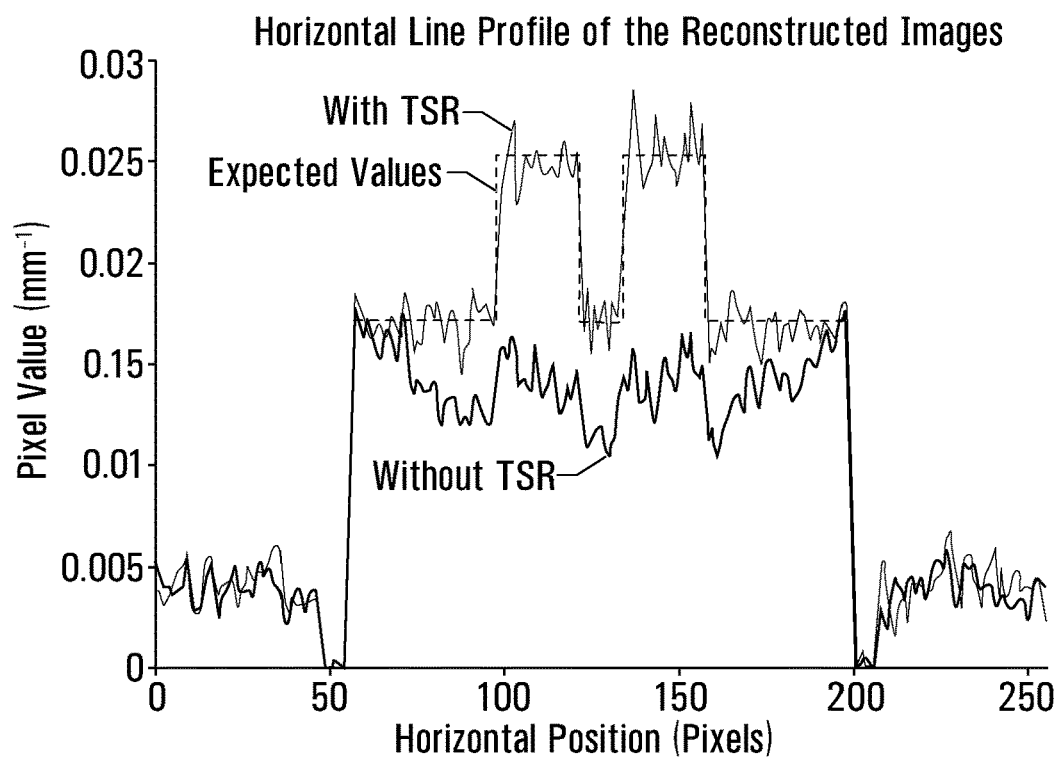
FIG. 13 is a horizontal line profile of the reconstructed images in FIG. 11A without TSR and with TSR, showing also the expected values based on the phantom structure.

As shown by the horizontal line profile in the center of the image of FIG. 13, the CNR is doubled and the cup artifact is greatly reduced. The inaccuracies of the reconstructed values, inherent to scatter noise, are also reduced. An image was reconstructed with a dose four times smaller, the CNR after TSR was the same as the original image with full dose and the cup artifact was still reduced, but photon deprivation artifacts appeared.

Figure 10:
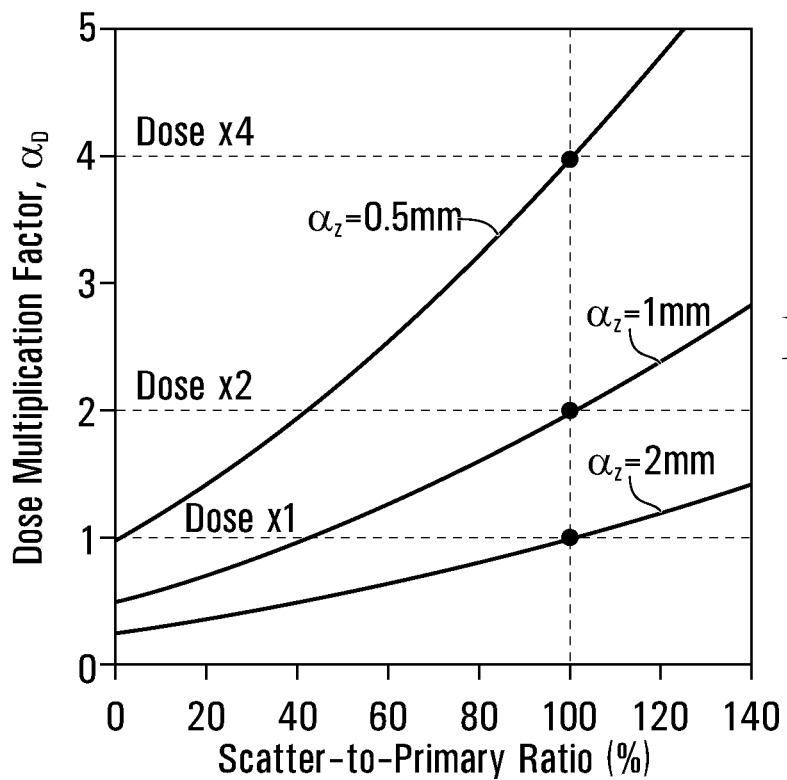
FIG. 10 is a graph showing dose multiplication factor required to correct the CNR degradation caused by scatter noise as a function of SPR (Siewerdsen and Jaffray 2001)

With TSR implemented to remove scattered photons, the expected dosage reduction as a function of SPR reduction is shown in FIG. 10. The degradation of CNR can be corrected with either an increase of dose or an increase in pixel size, shown in FIG. 10 as $a_z$, however such increase also reduces spatial resolution. Therefore, to correct for a scatter noise of 100% SPR and keep the same spatial resolution, a four-fold increase in dose is required. If the total time resolution is short enough to completely mitigate the effect of scatter noise, it could be possible to divide the dose by four. With a time resolution of around 100 ps, the expected dose reduction for an abdomen scan is more than 50%.

Figure 14A:
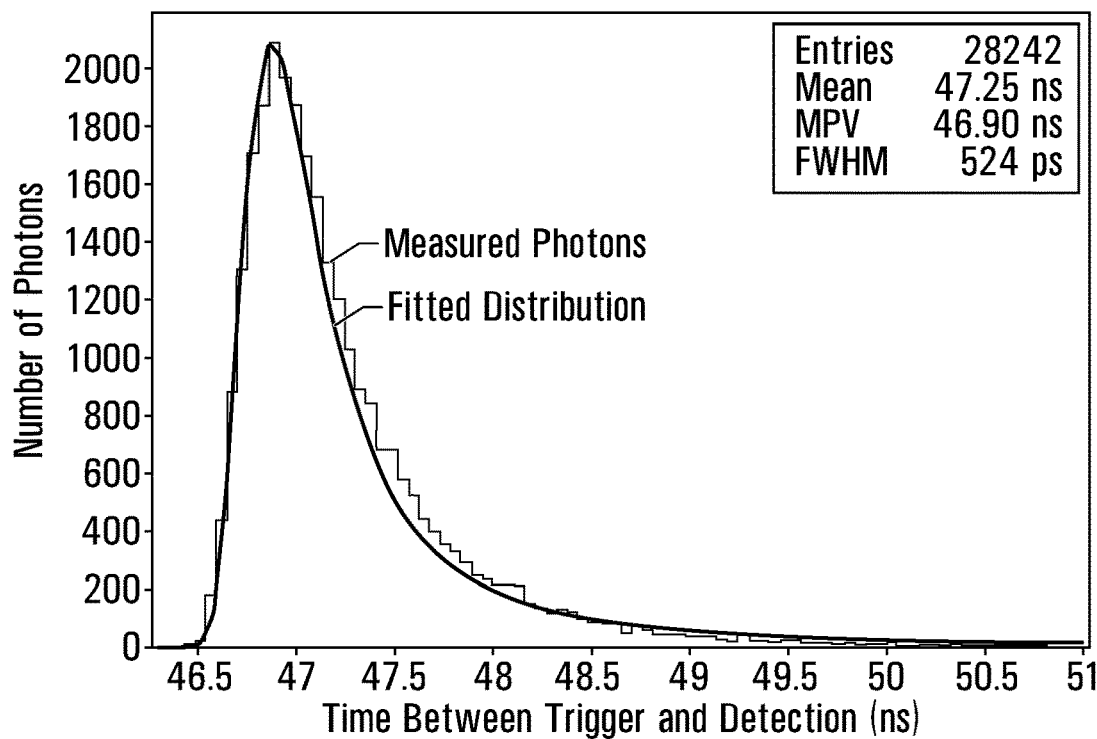
FIG. 14A is a histogram of the number of photons measured experimentally with nothing between the source and the detectors according to the time between the source trigger and the detection fitted with a Landau distribution.
Figure 14B:
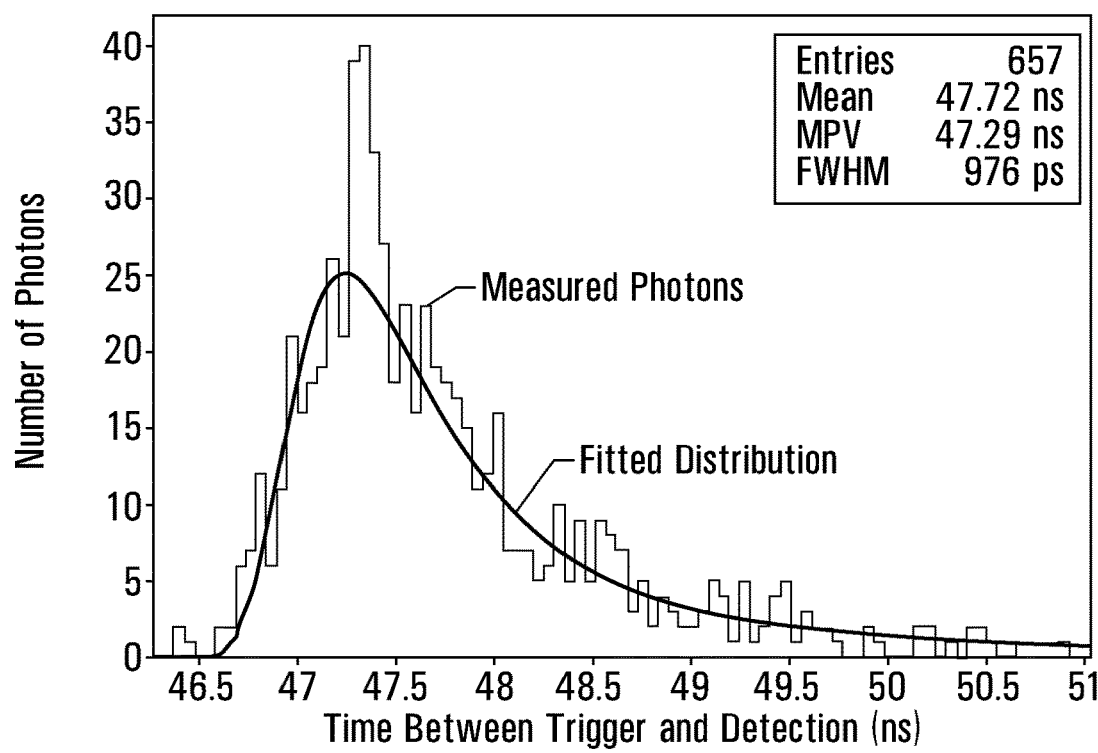
FIG. 14B is a histogram of the number of photons measured experimentally with a 4 cm thick beam-blocker between the source and the detectors according to the time between the source trigger and the detection fitted with a Landau distribution.

An experiment was conducted to confirm the feasibility of observing TOF differences between scattered and transmitted photons. A 3×3 mm² silicon photomultiplier (SiPM) covered by a 500 μm thick lutetium-yttrium oxyorthosilicate (LYSO) crystal was placed 38 cm in front of a pulsed X-ray source (Hamamatsu with mean photon energy of 15 keV and pulse width of 60 ps. Two measurements were made: one with nothing between the source and the detector and one with a 40 mm thick aluminum beam blocker. FIG. 14A shows the time between trigger and detection (TPSF) without the blocker, while FIG. 14B shows the time between trigger and detection with the blocker. 657 photons were detected after an acquisition of 36 hours. Once fitted with a Landau distribution, the most probable value (MPV) of the TOF with the beam blocker is 390 ps later than the MPV without the beam blocker, which correspond to an increase of travel path of about 12 cm. This fits with the expected increase of travel path needed to circle the beam blocker by scattering on the X-ray enclosure. No TOF correction was made for the energy of the detected photons. Higher energy photons were detected earlier, however, the increased TOF of scattered photons is observed at all energy levels at around 400 ps. Dark counts and double detections were removed from both measurements.

The X-ray source is responsible for emitting X-rays. The first X-ray sources were vacuum tubes (so-called X-ray tubes). It is with such devices that Roentgen accidentally discovered X-rays. Their construction is rather simple as illustrated schematically in FIG. 15. At one end of a vacuum tube is a filament heated at high temperature by an electric current (voltage Uh). Through the physical process of thermionic emission, electrons are ejected from the filament (so-called the hot cathode, made out of metal, typically tungsten). At the other end of the tube is a little plate (the anode also often made of tungsten) onto which the electrons are directed. A high voltage (Ua) electric field is established between the cathode and the anode for accelerating the electrons from the cathode to the anode. When the electrons impinge onto the anode, they are rapidly decelerated as they slowdown in the metal and X-ray photons are emitted through the process of Bremsstrahlung (from the German literally meaning braking radiation). It is a consequence of the laws of electromagnetism that when a charged particle is accelerated (or decelerated), it emits radiation, in the present case X-ray radiation. For a given high voltage between the cathode and the anode, the emitted X photons have energies that span a given range, so-called the energy spectrum of the source. A source that emits X photons of only one energy is called monochromatic, otherwise it is called polychromatic (this terminology is in analogy with visible photons for which different energies correspond to different colors—chroma)

Another means for producing X-rays is by bending radially a beam of electrons, i.e. when the electrons accelerate perpendicular to their velocity. This occurs for instance in synchrotrons using bending magnets. When the electrons travel at non-relativistic (resp. relativistic) speeds, then the radiation is called cyclotron (resp. synchrotron) radiation. Because of the great control of acceleration in synchrotrons, these are able to produce highly monochromatic X-rays. However, synchrotrons and cyclotrons are large infrastructures that are not viable for integration in commercial medical imaging devices.

In conventional X-ray tubes, the stream of X photons is continuous, but for the purposes of the present invention, very short pulses (or bursts) of X-rays of the order of at most a few tens of picoseconds are needed. Synchrotrons are able to produce such pulses, but these are too massive infrastructures for commercial imaging devices as said above. An alternative for obtaining short X-ray pulses is via X-ray emission from femtosecond laser-produced plasmas on solid surfaces (Von Der Linde et al. 2001). In this approach, an ultra-short high intensity laser pulse is focused onto a metallic target which rips out electrons from the metal and accelerates the electrons back towards the metal target where they decelerate, thus producing short X-ray bursts. Another approach is through high-order harmonic generation in gases, which resorts to intense ultra-short laser pulses. This approach can be carried out in gas-filled hollow fibers (Von Der Linde et al. 2001). These approaches can be foreseen to be amenable to reasonable sizes for integration in medical imaging devices since ultra-short pulse laser technology is nowadays highly compact.

Another approach to generate ultra-short X-ray pulses is one that has been developed for fluorescence lifetime measurements, whereby fluorescence is induced by X-ray excitation (Derenzo et al. 1994; Moses et al. 1995). In such a pulsed X-ray source, short pulses of light (<100 ps full-width at half maximum—FWHM) emitted by a pulsed laser diode are directed onto a light sensitive photocathode that emits short bursts of electrons with each light pulse impinging onto it (FIG. 16). The electrons are then amplified or not and accelerated towards an anode as in conventional X-ray tubes described above. Yet another approach to generate short X-ray pulses is to use an X-ray tube in which the electron beam can be very rapidly deflected as in a streak camera, with an electric pulsed field in such a way that it strikes the anode for a very short time interval in which bremsstrahlung X-rays can be generated.

Another solution to generate X-ray pulses is to replace the photocathode with carbon nanotubes (CNT) as described in (Parmee et al. 2015). The CNTs are plated on top of the cathode as an electron emitter with the capability to be gated faster than the cathode alone directly with an electric signal (FIG. 17) and operating at lower temperature.

Different technology configurations can support embodiments of the invention and are not limited to the example described below.

The detector is among the important components to consider in the deployment of the technology. There are two main detection principles: Direct conversion and indirect conversion. While the direct conversion of X photons in materials such as germanium or silicon is very attractive for high energy resolution, indirect conversion can be a preferred avenue thanks to its lower operating voltage and its proven better timing resolution. The electron/hole mobility in direct conversion detectors coupled to the detector thickness do not currently allow obtaining timing performance in the tens of picoseconds as can be desired. Alternatively, the use of a thin scintillator able to stop an X photon coupled to a high-speed photodetector such as a silicon photomultiplier (SiPM) or all its digital derivatives is a good candidate for a complete system with timing performance under 100 ps.

Although an indirect conversion mechanism is to be preferred, it must be intimately coupled to an adequate gating mechanism. The brute force approach would be to timestamp every individual photon and to provide the information to a digital signal processor able to process, in real-time, the relevant information for image reconstruction. This processor could be integrated in 2.5D or 3D electronics along with the photodetector or located remotely outside the scanner. The processing algorithms can be of any form from gating, filtering, up to machine learning. However, this approach will require a large data bandwidth and other approaches can be used.

In order to reduce the bandwidth, an adjustable and delayed trigger can be distributed in the scanner. This trigger can open a time window where all photons striking the detector in the time window are timestamped or counted. The information can still be sent to a local or a remote digital processor with the goal to extract the relevant information to be fed to the image reconstruction algorithm. The trigger can be self-adjusted from the center of the detector panel to the periphery or manually adjusted with programmable or fixed delay lines to take into account the source to flat panel distance variation form the center to the periphery. In the former case, each pixel has a communication link with its adjacent neighbor while in the latter case, a system calibration is mandatory.

It would also be possible to use energy integration detectors to implement the discrimination between ballistic and scattered photons by either turning on and off the energy integration according to the time window or by reading such detectors at the beginning and at the end of the time window to only measure the energy of ballistic photons.

Figure 18:
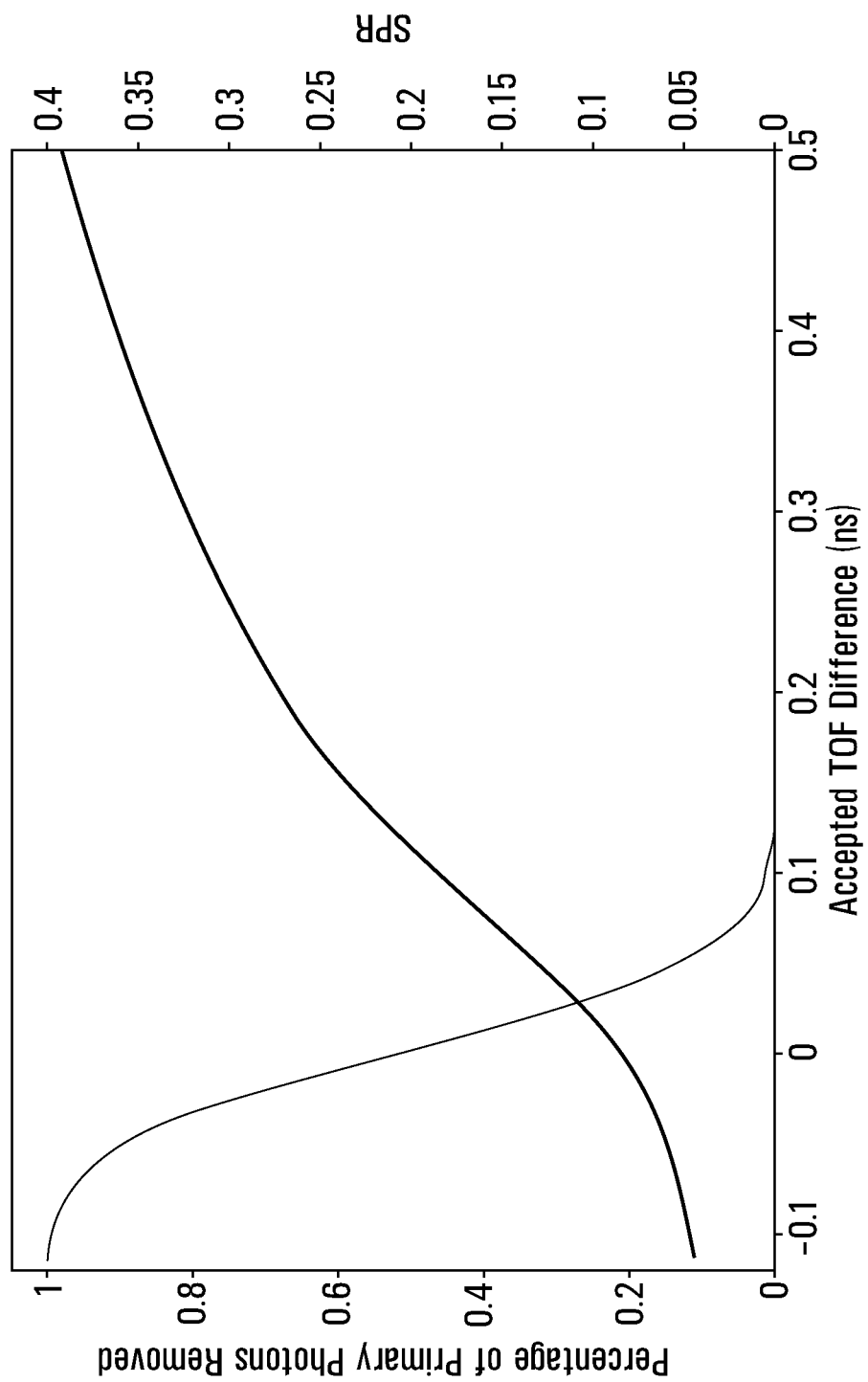
FIG. 18 is a double graph showing the decrease in percentage of primary photons removed as a function of accepted time-of-flight difference in nanoseconds and the increase in SPR as a function of accepted time-of-flight difference in nanoseconds.

Optimizing TOF-X-ray imaging (whether 2D or 3D) revolves around one central idea: having the right gate width. Ideally the gate width is selected to be narrow enough to allow almost all the ballistic photons but remove the maximum number of scattered photons. To achieve this, the impact of every component of the system on the gate width must be considered. Ideally, the gate width would be almost zero, but the source pulse width must then be short enough to avoid removing ballistic photons. Parameters leading to errors in TOF measurements, such as the pulse width of the X-ray source (and in some cases the sharpness of the rising edge of the pulse) or the timing resolution of the detectors, widen the response of the system to ballistic photons. To keep almost all ballistic photons, the gate must be widened even if the errors increase, but doing this reduces the proportion of scattered photons being removed. However, since removing part of the ballistic photons reduces the SNR while removing more scattered photons increases the CNR, the gate width can be chosen more conservatively or more aggressively according to whether SNR or CNR is driving the dose. On one hand, increasing the SNR is particularly important in very low dose applications and in imaging systems with a naturally high contrast such as inorganic imaging. On the other hand, CNR will drive the dose up in biological tissue imaging with only small density differences such as in breast imaging. The quantity of ballistic photons removed and scattered to primary ratio according to the chosen gate in a system with 100 ps of total time resolution is shown in FIG. 18.

Reducing the total time resolution is one of the most important design aspects of TOF-X-ray imaging (whether 2D or 3D). The errors caused by each component of the system are added together in quadrature. Thus, reducing the pulse width and the timing resolution of the detectors is equally important to increase the efficiency of discrimination. If both effects are reduced to under 10 ps, the spatial uncertainty of the emission (the size of the focal spot of the source) and of the detection (size of the detector and error on positioning) will also have to be optimized since this affects the expected TOF for ballistic photons used as a comparison for the discrimination. Jitter between detectors will also increase the error on the measurements and will have to be reduced to a minimum.

The present method uses the maximum possible TOF between the source and a pixel for discriminating ballistic and scattered X photons. However, to further optimize this method, it could be useful, in large pixel-size systems, to use the most likely depth of detection for the window. Doing this will reduce the number of ballistic photons that are retained, but should reduce the measured SPR.

Embodiments can be implemented in a variety of systems. The following have been identified as potential interesting applications of TOF-X-ray imaging (whether 2D or 3D):
1. Pediatric (where dose of radiation can be reduced to acceptable levels);
2. Pre-clinical (where spatial resolution can be improved due to reduced CNR);
3. Dental care (where dose and form factor are important);
4. Bariatric patients (where contrast is a problem);
5. Extremities (form factor and dose);
6. Interventional radiology (form factor, dose and resolution);
7. Gating imaging.

These systems require different adjustments in their design options (or optimization) for dose, spatial resolution, contrast and form factor as indicated in parentheses above. X-ray imaging (whether 2D or 3D) is rarely used for pediatric patients because of the high radiation dose associated with current X-ray imaging procedures. The method presented herein, by reducing the dose allows for use of the technique for this application. Scan of extremities, dental care and interventional radiology can also be optimised for dose to reduce the impact of the repeated use required by those applications. For this, the system can be designed to further reduce the dose notably by reducing the gate size according to the CNR and SNR requirements, and increase sensitivity. Imaging naturally high contrast volume, such as in dental care, will generally require optimizing for SNR while low contrast imaging, such as breast imaging, will require optimizing for CNR. The window can be modified according to the required needs, for instance looking for fractured bones requires a large window to increase SNR, but scanning the same area for potential tumors requires a small window to increase CNR.

Spatial resolution is particularly important for both preclinical and interventional radiology. A significantly higher spatial resolution can be obtained by using embodiments as described herein in conjunction with single photon avalanche diodes (SPADs) detectors to precisely pinpoint the location of the interaction of the X-ray with the detectors. The quality of the discrimination, along with the spatial resolution, can also be improved by using a magnification process such as increasing the distance between the volume of interest and the detector system.

Scanning bariatric patients requires photons of higher energies than the standard range of energy used in X-ray imaging (whether 2D or 3D) and yields a lower contrast image. TSR is particularly useful for scanning bariatric patients since larger volumes generate more scatter noise that is easier to remove with our approach since the photons generally scatter more than once in the subject in those cases. Optimizing for contrast, notably by choosing an aggressive gate, smaller than the total time resolution of the system, could even further help to scan bariatric patients.

The embodiments described herein can allow the usage of cone-beam computed tomography with even larger volumes. Cone-beam CT has a big advantage over standard helicoidal fan beam CT mostly used nowadays since it does not require linear translation of the patient. The simplicity of the mechanical parts of cone-beam CT reduces the form factor of the scanner, a necessity to use such system directly in an operating theater.

Finally, embodiments of the invention can be well suited for gated imaging where the X-ray source could be turned on and off according to an external signal such as respiratory gating or cardiac to avoid motion artifacts and better visualise the organ. CNR could then be better improved in such circumstances.

REFERENCES

Barrett, Julia F, and Nicholas Keat. 2004. "EDUCATION EXHIBIT Artifacts in CT: Recog-Nition and Avoidance 1." RadioGraphics. www.rsna.org (Oct. 29, 2018).

Derenzo, S. E. et al. 1994. "Design of a Pulsed X-Ray System for Fluorescent Lifetime Measurements with a Timing Accuracy of 109 Ps." IEEE Transactions on Nuclear Science.

Von Der Linde, D et al. 2001. Generation and Application of Ultrashort X-Ray Pulses. http://www.ilp.physik.uni-essen.de/vonderLinde/Publikationen/vonderLinde01LPB19_15.pdf (Oct. 29, 2018).

Martin, Cj. 2007. "The Importance of Radiation Quality for Optimisation in Radiology." Biomedical imaging and intervention journal 3(2): e38. http://www.ncbi.nlm.nih.gov/pubmed/21614278 (Oct. 29, 2018).

Moses, W. W. et al. 1995. "Scintillator Characterization Using the LBL Pulsed X-Ray Facility." Radiation Measurements 24(4): 337-41. https://www.sciencedirect.com/science/article/abs/pii/135044879400111D (Oct. 29, 2018).

Parmee, Richard J, Clare M Collins, William I Milne, and Matthew T Cole. 2015. "X-Ray Generation Using Carbon Nanotubes." Nano Convergence 2(1): 1. http://www.nanoconvergencejournal.com/content/2/1/1 (Oct. 29, 2018).

Rui, Xue et al. 2014. "Optimal KVp Selection for Contrast CT Imaging Based on a Projection-Domain Method." *Conference proceedings. International Conference on Image Formation in X-Ray Computed Tomography* 2014: 173-77. http://www.ncbi.nlm.nih.gov/pubmed/26413581 (Oct. 22, 2018).

Siewerdsen, Jeffrey H., and David A. Jaffray. 2001. "Cone-Beam Computed Tomography with a Flat-Panel Imager: Magnitude and Effects of x-Ray Scatter." *Medical Physics* 28(2): 220-31. http://doi.wiley.com/10.1118/1.1339879 (Apr. 25, 2017).

Webb, Steve. 1988. *The Physics of Medical Imaging*. Hilger. https://www.crcpress.com/The-Physics-of-Medical-Imaging/Webb/p/book/9781439822081 (Apr. 2, 2017).

Wikimedia Commons. 2010. "Coolidge Side-Window Tube (Scheme) C: Filament/Cathode (−) A: Anode (+) Win and Wout: Water Inlet and Outlet of the Cooling Device." *X-Ray Tube*: https://en.wikipedia.org/wiki/X-ray_tube#/media/Fi.

What is claimed is:

1. An X-ray imaging apparatus comprising:
a pulsed X-ray source having a control signal, wherein said pulsed X-ray source produces a fan or a cone shaped beam;
a time-sensitive X-ray detector having a time-dependent X-ray photon detection signal output and for one of:
providing for each photon detected at each pixel element a time of detection signal; and
being responsive to a gate signal controlling a time when photon detection is enabled or disabled;
wherein said time-sensitive X-ray detector comprises an X-ray sensitive scintillator and a light sensor array coupled with said scintillator for measuring X-ray detection events in said scintillator;
a processor, connected to said control signal and said time-dependent X-ray photon detection signal output, having an output for providing a measure of ballistic photons with a reduction in a measurement of scattered photons received by said time-sensitive detector;

wherein said time-sensitive X-ray detector is arranged with respect to said pulsed X-ray source so as to provide a different time of flight for said ballistic photons as a function of a pixel location within said time-sensitive X-ray detector; and wherein said processor provides said measure of ballistic photons with said reduction in the measurement of scattered photons received by said time-sensitive detector using different timing as a function of location of said pixels.

2. The apparatus as defined in claim 1, wherein said pulsed X-ray source comprises a high voltage source, electrodes connected to said high voltage source for accelerating electrons, and an X-ray emitting target material arranged to receive said electrons following acceleration by said electrodes so as to produce a pulse of X-rays.

3. The apparatus as defined in claim 2, wherein said pulsed X-ray source comprises:
a pulsed laser source responsive to said control signal;
a photoelectric material arranged to receive a light pulse from said pulsed laser source and to emit a burst of electrons in response thereto;
wherein electrodes are arranged to accelerate said burst of electrons.

4. The apparatus as defined in claim 3, wherein said photoelectric material is at least a part of a cathode of said electrodes.

5. The apparatus as defined in claim 2, wherein said pulsed X-ray source comprises deflection electrodes for steering said electrons accelerated by said electrodes connected to said high voltage source to controllably hit said X-ray emitting target material.

6. The apparatus as defined in claim 2, wherein said electrodes connected to said high voltage source comprise a gated carbon nanotube cathode.

7. The apparatus as defined in claim 1, wherein said time-sensitive X-ray detector is responsive to a gate signal controlling a time when photon detection is enabled or disabled, and said processor collects, when in use, X-ray photons detected within different time frames with respect to said control signal and determine said measure of ballistic photons with a reduction in the measurement of scattered photons received by said time-sensitive detector through subtraction of said X-ray photons detected within different time frames.

8. The apparatus as defined in claim 1, wherein said gate signal controlling said time when photon detection is enabled or disabled is a pulsed gate signal.

9. The apparatus as defined in claim 1, wherein said apparatus is operative to obtain an image with a given contrast to noise ratio (CNR) while delivering a dosage of X-rays to a typical human abdominal region of at least 20 cm thickness that is at least 50% less than when-said time-sensitive X-ray detector and said processor having an output for providing, when in use, a measure both ballistic and scattered photons without a reduction in the measurement of scattered photons from said pulsed X-ray source.

10. The apparatus as defined in claim 9, wherein said delivered dosage of said X-rays to said typical human abdominal region is at least 50% lower.

11. The apparatus as defined in claim 1, wherein said pulsed X-ray source produces a cone beam and said a time-sensitive X-ray detector is arranged to detect a 2D array of pixels.

12. The apparatus as defined in claim 1, wherein a rise time of a pulse emitted by said pulsed X-ray source is less than 0.15 nanoseconds, and a response time of a combination of said pulsed X-ray source and said time-sensitive detector is less than 0.9 nanoseconds.

13. The apparatus as defined in claim 1, wherein said processor for measuring an impulse response time of a combination of said pulsed X-ray source and said time-sensitive detector to obtain a measure of ballistic photons without an object or patient between said pulsed X-ray source and said time-sensitive detector and to derive therefrom and store in memory a gate parameter for said measure of ballistic photons with a reduction in the measurement of scattered photons received by said time-sensitive detector when thereafter measuring objects or patients that provide scatter.

14. A method of acquiring a medical diagnostic image of a human patient comprising using an apparatus as defined in claim 1 to obtain an image of a region of interest and having a contrast-to-noise ratio using X-rays of a given energy, wherein an amount of radiation delivered to said patient is about 60% or less of an amount of radiation delivered to a same patient for continuous, polychromatic X-ray imaging of said region of interest using said given energy of X-rays.

15. The method as defined in claim 14, wherein said amount of radiation delivered to said patient is about 30% or less of an amount of radiation delivered to a same patient for continuous, polychromatic X-ray imaging of said region of interest using said given energy of X-rays.

16. The apparatus as defined in claim 1, wherein a rise time of a pulse emitted by said pulsed X-ray source is less than 0.15 nanoseconds, and a response time of a combination of said pulsed X-ray source and said time-sensitive detector is less than 0.3 nanoseconds.

17. An X-ray imaging apparatus comprising:
a pulsed X-ray source having a control signal;
a time-sensitive X-ray detector having a time-dependent X-ray photon detection signal output;
a processor, connected to said control signal and said time-dependent X-ray photon detection signal output, having an output for providing, when in use, a measure of ballistic photons with a reduction in a measurement of scattered photons received by said time-sensitive detector; and
wherein said time-sensitive X-ray detector is arranged with respect to said pulsed X-ray source so as to provide a different time of flight for said ballistic photons as a function of a pixel location within said time-sensitive X-ray detector, wherein said processor provides said measure of ballistic photons with said reduction in the measurement of scattered photons received by said time-sensitive detector using different timing as a function of location of said pixels.

18. An X-ray imaging apparatus comprising:
a pulsed X-ray source having a control signal;
a time-sensitive X-ray detector having a time-dependent X-ray photon detection signal output;
a processor, connected to said control signal and said time-dependent X-ray photon detection signal output, having an output for providing a measure of ballistic photons with a reduction in a measurement of scattered photons received by said time-sensitive detector and to generate a 2D and/or a 3D image from said measure;
wherein said apparatus is operative to obtain said image with a given contrast to noise ratio (CNR) while delivering a dosage of X-rays that is at least 30% lower to a typical human abdominal region of at least 20 cm thickness than when continuous X-rays of a same energy are used in a similarly-structured continuous X-ray imaging apparatus.

\* \* \* \* \*